(12) United States Patent
Sato et al.

(10) Patent No.: US 8,952,247 B2
(45) Date of Patent: Feb. 10, 2015

(54) PHOTOELECTRIC CONVERTER AND SOLAR CELL USING THE SAME

(75) Inventors: Yoshiharu Sato, Sagamihara (JP); Eiichi Nakamura, Bunkyo-ku (JP); Takaaki Niinomi, Bunkyo-ku (JP); Yutaka Matsuo, Chuo-ku (JP); Masahiko Hashiguchi, Kitakyushu (JP)

(73) Assignee: Mitsubishi Chemical Corporation, Tokyo (JP)

( * ) Notice: Subject to any disclaimer, the term of this patent is extended or adjusted under 35 U.S.C. 154(b) by 1184 days.

(21) Appl. No.: 12/668,141

(22) PCT Filed: Jul. 3, 2008

(86) PCT No.: PCT/JP2008/062054
§ 371 (c)(1),
(2), (4) Date: Jan. 7, 2010

(87) PCT Pub. No.: WO2009/008323
PCT Pub. Date: Jan. 15, 2009

(65) Prior Publication Data
US 2011/0005597 A1   Jan. 13, 2011

(30) Foreign Application Priority Data

Jul. 9, 2007  (JP) ................................. 2007-179271
Feb. 1, 2008  (JP) ................................. 2008-022919

(51) Int. Cl.
*H01L 31/04*   (2006.01)
*H01L 51/00*   (2006.01)
(Continued)

(52) U.S. Cl.
CPC ............. *H01L 51/0094* (2013.01); *B82Y 10/00* (2013.01); *C07F 7/0809* (2013.01); *H01L 51/0036* (2013.01); *H01L 51/0047* (2013.01); *H01L 51/0037* (2013.01);
(Continued)

(58) Field of Classification Search
USPC .................................... 136/263; 977/734, 735
See application file for complete search history.

(56) References Cited

U.S. PATENT DOCUMENTS 6,198,091 B1 * 3/2001 Forrest et al. ............... 250/214.1
2005/0224113 A1 * 10/2005 Xue et al. ....................... 136/263
(Continued)

FOREIGN PATENT DOCUMENTS

JP         5-335614     12/1993
JP         7-89972      4/1995
(Continued)

OTHER PUBLICATIONS

Extended European Search Report issued Jul. 13, 2011, in European Patent Application No. 08777806.4.
(Continued)

*Primary Examiner* — Matthew Martin
(74) *Attorney, Agent, or Firm* — Oblon, Spivak, McClelland, Maier & Neustadt, L.L.P.

(57) ABSTRACT

The present invention provides a photoelectric conversion device having at least a fullerene derivative as an electron acceptor and a compound as an electron donor between a pair of electrodes, wherein the fullerene derivative has 2 to 4 organic groups which each independently have 1 to 50 carbon atoms, and wherein when the fullerene derivative has two organic groups, these organic groups do not bind to each other to form a ring.

17 Claims, 1 Drawing Sheet

(51) Int. Cl.
*B82Y 10/00* (2011.01)
*C07F 7/08* (2006.01)
*H01L 51/42* (2006.01)

(52) U.S. Cl.
CPC ............ *H01L 51/424* (2013.01); *Y02E 10/549* (2013.01); *Y10S 977/734* (2013.01); *Y10S 977/735* (2013.01)
USPC ............ 136/263; 136/252; 977/734; 977/735

(56) References Cited

U.S. PATENT DOCUMENTS

| | | | |
|---|---|---|---|
| 2007/0079867 A1* | 4/2007 | Chittibabu et al. | ........... 136/252 |
| 2009/0101200 A1 | 4/2009 | Nakamura et al. | |
| 2009/0118527 A1 | 5/2009 | Nakamura et al. | |
| 2009/0194158 A1 | 8/2009 | Nakamura et al. | |
| 2009/0308458 A1 | 12/2009 | Aramaki et al. | |
| 2010/0048934 A1 | 2/2010 | Nakamura et al. | |

FOREIGN PATENT DOCUMENTS

| | | |
|---|---|---|
| JP | 8-500701 | 1/1996 |
| JP | 8-222281 | 8/1996 |
| JP | 2003-212880 | 7/2003 |
| JP | 2003212881 A * | 7/2003 |
| JP | 2004-277736 | 10/2004 |
| JP | 2006-245073 | 9/2006 |
| JP | 2007-67115 | 3/2007 |
| WO | WO 94/05045 | 3/1994 |

OTHER PUBLICATIONS

C. J. Brabec, et al., "The influence of materials work function on the open circuit voltage of plastic solar cells", Thin Solid Films, vol. 403-404, XP-004430386, Feb. 1, 2002, pp. 368-372.
Jean Roncali, "Linear π-conjugated systems derivatized with $C_{60}$-fullerene as molecular heterojunctions for organic photovoltaics", Chemical Society Reviews, vol. 34, XP-55001583, Feb. 28, 2005, pp. 483-495.
Hideo Nagashima, et al., "Electronic Structures and Redox Properties of Silylmethylated C60", Tetrahedron, vol. 52, No. 14, 1996, pp. 5053-5064.
G. Yu, et al., "Polymer Photovoltaic Cells: Enhanced Efficiencies via a Network of Internal Donor-Acceptor Heterojunctions", Science, vol. 270, Dec. 15, 1995, pp. 1789-1791.
Masahiko Hashiguchi, et al., "Synthesis of Fullerene Derivatives as New Acceptor Materials and Photovoltaic Properties", The 87th Annual Meeting of the Chemical Society of Japan in Spring (2007), Mar. 12, 2007,1B9-41, 4 pages (with English translation).
T. Niinomi, et al., "Organic Photovoltaics Based on New Organo[C60]fullerenes (II)", The $68^{th}$ Autumn Lecture Meeting of the Japan Society of Applied Physics Gists of Speeches Prepared in Advance (2007 Autumn, Hokkaido Institute of Technology), 7p-ZN-2, Sep. 2007, p. 1261 (with English translation).
C. W. Tang., "Two-layer organic photovoltaic cell", Applied Physics Letters, vol. 48, No. 2, Jan. 13, 1986, pp. 183-185.
Yoko Abe, et al., "Synthesis and Properties of Fullerene Derivatives as New Materials for Organic Photovoltaic cell", The $88^{th}$ Annual Meeting of Chemical Society of Japan (2008), 4 L7-03, Mar. 12, 2008, 5 pages (with English translation).
Yoshiharu Sato, et al., "Organic photovoltaics based on solution-processed benzoporphyrin", Proc. of SPIE, vol. 6656, 2007, pp. 66560U-1 to 66560U-9.
Yoshiharu Sato, et al., "Organic photovoltaic Cell Based on benzoporphyrin with p-i-n. Junction", Proc. of SPIE, vol. 7052, 2008, pp. 70520J-1 to 70520J-9.
Yoko Abe, et al., "Regioselective Synthesis of 1,4 -Di(organo)[60]fullerenes and these Properties", The $55^{th}$ Symposium on Organometallic Chemistry, P2C-10, 2004, 4 pages (with English translation).
Yoko Abe, et al., "Synthesis and Properties of Silylmethyl[70]fullerene Derivatives (ERATO, JST, The Univ. of Tokyo)", The $89^{th}$ Annual Meeting of Chemical Society of Japan (2009), Mar. 30, 2009, 5 pages (with English translation).
Yutaka Matsuo, et al., "Columnar Structure in Bulk Heterojunction in Solution-Processable Three-Layered p-i-n Organic Photovoltaic Devices Using Tetrabenzoporphyrin Prercursor and Silymethyl[60]fullerene" J. Am. Chem. Soc., 2009, pp. 16048-16050.
Yutaka Matsuo, et al, "OHM", Energy & Electric Power, Feb. 12, 2010, 3 pages (with English translation).
Office Action issued Mar. 19, 2013, in Japanese Patent Application No. 2008-0174166, filed Jul. 3, 2008 w/English-language translation.
Office Action issued Sep. 30 2013, in Taiwanese Patent Application No. 20080125858, filed Jul. 9, 2008 w/English-language translation.

* cited by examiner

Light

Light

PHOTOELECTRIC CONVERTER AND SOLAR CELL USING THE SAME

TECHNICAL FIELD

The present invention relates to a photoelectric conversion device and a solar cell comprising the same. Specifically, the present invention relates to a photoelectric conversion device comprising a fullerene derivative as an electron acceptor and a compound as an electron donor and a solar cell comprising the same.

BACKGROUND ART

So far, solar cells, in which a photoelectric conversion device comprising an inorganic material such as silicon is used, have been put to practical use. When producing a photoelectric conversion device comprising polycrystalline silicon, high-purity silicon is essential, but its cost is relatively high.

On the other hand, in general, a photoelectric conversion device comprising an organic material can be more easily produced compared to the photoelectric conversion device comprising the inorganic material. Therefore, its production cost can be reduced. Examples of solar cells comprising the photoelectric conversion device comprising the organic material include dye-sensitized solar cells, and solar cells comprising an organic semiconductor material called "organic thin-film solar cell".

However, since electrolyte used in a typical dye-sensitized solar cell is usually a liquid (electrolytic solution), there may be a problem of such electrolytic solution leaking out or volatilizing from a space between a working electrode and an opposite electrode, etc. Thus, there is a problem that the photoelectric conversion device comprising the organic material has less durability compared to the photoelectric conversion device comprising the inorganic material.

Further, examples of the photoelectric conversion device comprising the organic material include: a photoelectric conversion device in which copper phthalocyanine as an electron donor is combined with a perylene derivative as an electron acceptor (C. W Tang, "Two-Layer organic photovoltaic cell", Applied Physics Letters, 1986, Vol. 48 (Non-patent Document 1)); and a photoelectric conversion device in which polyphenylene vinylene as an electron donor is combined with a fullerene derivative (G Yu et al., "Polymer Photovoltaic Cells: Enhanced Efficiencies via a Network of Internal Donor-Acceptor Heterojunctions", Science, 1995, Vol. 270 (Non-patent Document 2); Japanese National-phase PCT Laid-Open Patent Publication No. 8-500701 (Patent Document 1)).

However, the conversion efficiency of these photoelectric conversion devices is still low. For practical use, the conversion efficiency is desired to be further improved.

[Patent Document 1] Japanese National-phase PCT Laid-Open Patent Publication No. 8-500701

[Non-patent Document 1] C. W. Tang, "Two-Layer organic photovoltaic cell", Applied Physics Letters, 1986, Vol. 48

[Non-patent Document 2] G Yu et al., "Polymer Photovoltaic Cells: Enhanced Efficiencies via a Network of Internal Donor-Acceptor Heterojunctions", Science, 1995, Vol. 270

DISCLOSURE OF THE INVENTION

Problems to be Solved by the Invention

Under the above-described circumstances, for example, a photoelectric conversion device having high conversion efficiency, which can be produced at low cost, is desired.

Means for Solving the Problems

The present inventors found a photoelectric conversion device comprising a fullerene derivative having 2 to 4 organic groups which each independently have 1 to 50 carbon atoms and a compound as an electron donor between a pair of electrodes, and a solar cell comprising the device. Based on this finding, the present invention was achieved. The present invention provides a photoelectric conversion device and a solar cell as follows.

[1] A photoelectric conversion device having at least a fullerene derivative as an electron acceptor and a compound as an electron donor between a pair of electrodes, wherein the fullerene derivative has 2 to 4 organic groups which each independently have 1 to 50 carbon atoms, and wherein when the fullerene derivative has two organic groups, these organic groups do not bind to each other to form a ring.

[2] The photoelectric conversion device according to item [1], wherein the fullerene derivative has 2 or 3 organic groups which each independently have 1 to 50 carbon atoms.

[3] The photoelectric conversion device according to item [1] or [2], wherein the fullerene is at least one selected from the group consisting of fullerene $C_{60}$ and fullerene $C_{70}$.

[4] A photoelectric conversion device having at least a fullerene derivative as an electron acceptor represented by the following formula (1):

$$C_{60}(R^1)(R^2) \quad (1)$$

(wherein in formula (1): $R^1$ and $R^2$ are each independently an organic group having 1 to 50 carbon atoms; and $R^1$ and $R^2$ do not bind to each other to form a ring), and a compound as an electron donor between a pair of electrodes.

[5] A photoelectric conversion device having at least a fullerene derivative as an electron acceptor represented by any one of the following formulae (1A) to (1G):

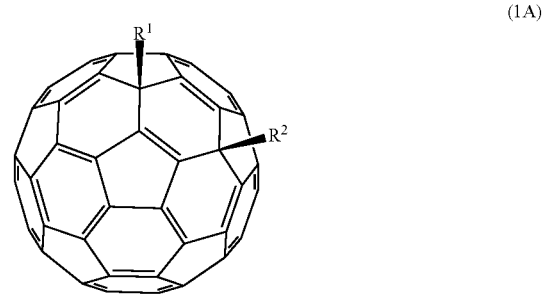

(1A)

-continued (1B) 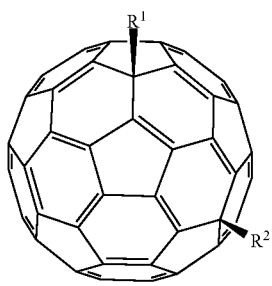

(1C) 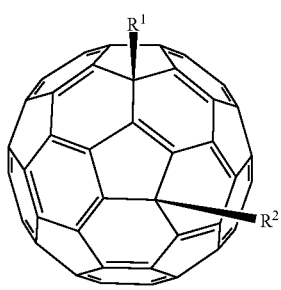

(1D) 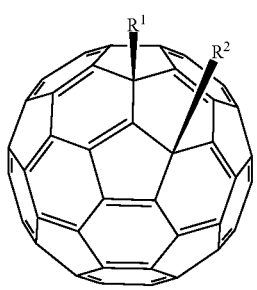

(1E) 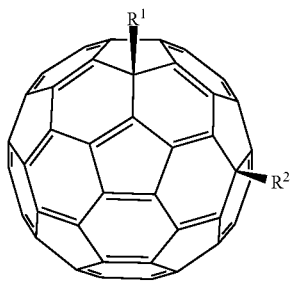

(1F) 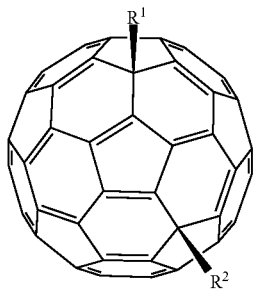

-continued (1G) 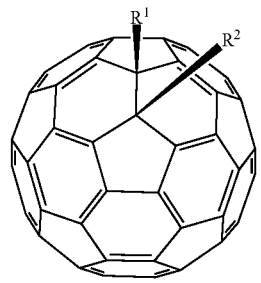

(wherein in the formulae (1A) to (1G): $R^1$ and $R^2$ are each independently an organic group having 1 to 50 carbon atoms; and $R^1$ and $R^2$ do not bind to each other to form a ring), and a compound as an electron donor between a pair of electrodes.

[6] A photoelectric conversion device having at least a fullerene derivative as an electron acceptor represented by the following formula (1A):

(1A)

(wherein in the formula (1A): $R^1$ and $R^2$ are each independently an organic group having 1 to 50 carbon atoms; and $R^1$ and $R^2$ do not bind to each other to form a ring), and a compound as an electron donor between a pair of electrodes.

[7] The photoelectric conversion device according to any one of items [1] to [6], wherein one or more of the organic groups having 1 to 50 carbon atoms are each independently a group comprising an aromatic ring.

[8] The photoelectric conversion device according to any one of items [1] to [7], wherein one or more of the organic groups having 1 to 50 carbon atoms are each independently a group represented by the following formula (3):

$$-(CH_2)_n-\underset{\underset{R^5}{|}}{\overset{\overset{R^3}{|}}{W}}-R^4 \quad (3)$$

(wherein in the formula (3): W is an atom belonging to group 4B of the periodic table; $R^3$, $R^4$ and $R^5$ are each independently an hydrogen atom, a hydrocarbon group having 1 to 50 carbon atoms, alkoxy or amino; and n is an integer from 1 to 10).

[9] The photoelectric conversion device according to item [8], wherein $R^3$, $R^4$ and $R^5$ are each independently a hydrocarbon group having 1 to 20 carbon atoms.

[10] The photoelectric conversion device according to item [8], wherein: $R^3$ and $R^4$ are an alkyl group having 1 to 3 carbon atoms; and $R^5$ is a hydrocarbon group having 1 to 20 carbon atoms.

[11] The photoelectric conversion device according to any one of items [8] to [10], wherein: n is an integer from 1 to 5; and W is Si.

[12] The photoelectric conversion device according to any one of items [4] to [6], wherein in the formula (1) or in the formulae (1A) to (1G): $R^1$ is a group represented by the following formula (31):

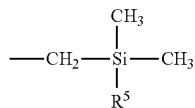
(31)

(wherein in the formula (31), $R^5$ is an alkyl group having 1 to 20 carbon atoms or phenyl); and $R^2$ is a group represented by the following formula (32):

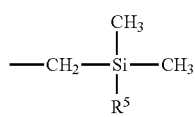
(32)

(wherein in the formula (32), $R^5$ is methyl or phenyl).

[13] The photoelectric conversion device according to any one of items [1] to [12], wherein the compound as the electron donor is a polymer compound.

[14] The photoelectric conversion device according to any one of items [1] to [12], wherein the compound as the electron donor is a heterocyclic polymer compound.

[15] The photoelectric conversion device according to any one of items [1] to [12], wherein the compound as the electron donor is a porphyrin compound or phthalocyanine compound.

[16] The photoelectric conversion device according to any one of items [1] to [12], wherein the compound as the electron donor is polythiophene or a copper phthalocyanine complex.

[17] The photoelectric conversion device according to any one of items [1] to [12], wherein the compound as the electron donor is tetrabenzoporphyrin.

[18] The photoelectric conversion device according to any one of items [1] to [17], which has a mixture layer comprising at least a fullerene derivative as an electron acceptor and a compound as an electron donor between a pair of electrodes.

[19] The photoelectric conversion device according to item [18], wherein the mixture layer is formed by applying a solution in which a mixture comprising a fullerene derivative as an electron acceptor and a compound as an electron donor is dissolved.

[20] The photoelectric conversion device according to item [18], wherein the mixture layer is formed by evaporating a fullerene derivative as an electron acceptor and a compound as an electron donor.

[21] The photoelectric conversion device according to any one of items [1] to [20], wherein a p-type semiconductor layer is formed between the mixture layer, which comprises the fullerene derivative as the electron acceptor and the electron donor, and a positive electrode.

[22] The photoelectric conversion device according to any one of items [1] to [21], wherein an n-type semiconductor layer is formed between the mixture layer, which comprises the fullerene derivative as the electron acceptor and the electron donor, and a negative electrode.

[23] A solar cell comprising the photoelectric conversion device according to any one of items [1] to [22].

Advantageous Effect of the Invention

According to a preferred embodiment of the present invention, a photoelectric conversion device having high conversion efficiency can be provided. Further, according to a preferred embodiment of the present invention, a photoelectric conversion device which can be easily produced at low cost can be provided.

EXPLANATIONS OF LETTERS OR NUMERALS

Figure 1:
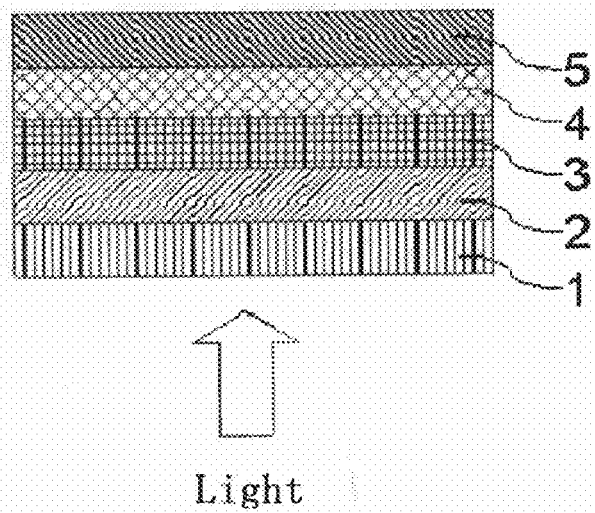
FIG. 1 is a diagram of the solar cell of Example 1.

1 . . . glass substrate
2 . . . ITO electrode (positive electrode)
3 . . . hole extraction layer
4 . . . mixture layer
5 . . . electrode (negative electrode)
6 . . . electron extraction layer
7 . . . p-type semiconductor layer
8 . . . n-type semiconductor layer

BEST MODE FOR CARRYING OUT THE INVENTION

1. Electron Donor and Electron Acceptor Included in the Photoelectric Conversion Device of the Present Invention Between a pair of electrodes which constitute the photoelectric conversion device of the present invention, an electron donor and an electron acceptor are provided. Between a pair of electrodes, the photoelectric conversion device of the present invention may have, for example, a laminate structure in which an electron donor layer is put on an electron acceptor layer, or may have a mixture layer consisting of a mixture comprising the electron donor and electron acceptor.

Further, the photoelectric conversion device of the present invention may have a plurality of pairs of electrodes.

1.1. Electron Acceptor Used in the Photoelectric Conversion Device

A compound to be used as an electron acceptor in the photoelectric conversion device of the present invention is a fullerene derivative having 2 to 4 organic groups which each independently have 1 to 50 carbon atoms (when the fullerene derivative has two organic groups, these organic groups do not bind to each other to form a ring). The fullerene derivative used as the electron acceptor in the photoelectric conversion device of the present invention is preferably a fullerene derivative having 2 or 3 organic groups which each independently have 1 to 50 carbon atoms, and it is desired that the fullerene is at least one selected from the group consisting of fullerene $C_{60}$ and fullerene $C_{70}$. A fullerene derivative represented by formula (1) above is more preferred. Among fullerene derivatives represented by formula (1) above, a fullerene derivative represented by any one of formulae (1A) to (1G) is preferred, and a fullerene derivative represented by formula (1A) is particularly preferred.

Note that the fullerene derivative used as the electron acceptor in the photoelectric conversion device of the present invention may be one type of fullerene derivative or may comprise a plurality of types of fullerene derivatives.

1.1.1. Fullerene $C_{60}$ Derivative

One embodiment of the fullerene derivative used as the electron acceptor in the photoelectric conversion device of the present invention is a fullerene $C_{60}$ derivative. Among fullerene $C_{60}$ derivatives, a fullerene derivative represented by formula (1) is preferred, and a fullerene derivative represented by any one of formulae (1A) to (1G) is more preferred. Note that $R^1$ and $R^2$ in the formulae (1A) to (1G) are each independently an organic group having 1 to 50 carbon atoms.

In the formula (1) or the formulae (1A) to (1G), it is preferred that $R^1$ and $R^2$ each independently represent a hydrogen atom, a substituted or unsubstituted $C_1$-$C_{20}$ hydrocarbon group, a substituted or unsubstituted $C_1$-$C_{20}$ alkoxy group, a substituted or unsubstituted $C_6$-$C_{20}$ aryloxy group, a substituted or unsubstituted amino group, a substituted or unsubstituted silyl group, a substituted or unsubstituted alkylthio group (—$SY^1$: in the formula, $Y^1$ is a substituted or unsubstituted $C_1$-$C_{20}$ alkyl group), a substituted or unsubstituted arylthio group (—$SY^2$: in the formula, $Y^2$ is a substituted or unsubstituted $C_6$-$C_{18}$ aryl group), a substituted or unsubstituted alkylsulfonyl group (—$SO_2Y^3$: in the formula, $Y^3$ is a substituted or unsubstituted $C_1$-$C_{20}$ alkyl group), or a substituted or unsubstituted arylsulfonyl group (—$SO_2Y^4$: in the formula, $Y^4$ is a substituted or unsubstituted $C_6$-$C_{18}$ aryl group).

In the present specification, the hydrocarbon group of the "$C_1$-$C_{20}$ hydrocarbon group" may be a saturated or unsaturated acyclic group or a saturated or unsaturated cyclic group. When the $C_1$-$C_{20}$ hydrocarbon group is acyclic, it may be linear or branched. The "$C_1$-$C_{20}$ hydrocarbon group" includes $C_1$-$C_{20}$ alkyl group, $C_2$-$C_{20}$ alkenyl group, $C_2$-$C_{20}$ alkynyl group, $C_4$-$C_{20}$ alkyldienyl group, $C_6$-$C_{18}$ aryl group, $C_7$-$C_{20}$ alkylaryl group, $C_7$-$C_{20}$ arylalkyl group, $C_4$-$C_{20}$ cycloalkyl group, $C_4$-$C_{20}$ cycloalkenyl group, and ($C_3$-$C_{10}$ cycloalkyl) $C_1$-$C_{10}$ alkyl group.

In the present specification, the "$C_1$-$C_{20}$ alkyl group" is preferably $C_1$-$C_{10}$ alkyl group, and more preferably $C_1$-$C_6$ alkyl group. Examples of alkyl groups include, but are not limited to, methyl, ethyl, propyl, isopropyl, n-butyl, sec-butyl, tert-butyl, pentyl, hexyl, and dodecanyl.

In the present specification, the "$C_2$-$C_{20}$ alkenyl group" is preferably $C_2$-$C_{10}$ alkenyl group, and more preferably $C_2$-$C_6$ alkenyl group. Examples of alkenyl groups include, but are not limited to, vinyl, allyl, propenyl, isopropenyl, 2-methyl-1-propenyl, 2-methylallyl, and 2-butenyl.

In the present specification, the "$C_2$-$C_{20}$ alkynyl group" is preferably $C_2$-$C_{10}$ alkynyl group, and more preferably $C_2$-$C_6$ alkynyl group. Examples of alkynyl groups include, but are not limited to, ethynyl, propynyl, and butynyl.

In the present specification, the "$C_4$-$C_{20}$ alkyldienyl group" is preferably $C_4$-$C_{10}$ alkyldienyl group, and more preferably $C_4$-$C_6$ alkyldienyl group. Examples of alkyldienyl groups include, but are not limited to, 1,3-butadienyl.

In the present specification, the "$C_6$-$C_{18}$ aryl group" is preferably $C_6$-$C_{10}$ aryl group. Examples of aryl groups include, but are not limited to, phenyl, 1-naphthyl, 2-naphthyl, indenyl, biphenyl, anthryl, and phenanthryl.

In the present specification, the "$C_7$-$C_{20}$ alkylaryl group" is preferably $C_7$-$C_{12}$ alkylaryl group. Examples of alkylaryl groups include, but are not limited to, o-tolyl, m-tolyl, p-tolyl, 2,3-xylyl, 2,4-xylyl, 2,5-xylyl, o-cumenyl, m-cumenyl, p-cumenyl, and mesityl.

In the present specification, the "$C_7$-$C_{20}$ arylalkyl group" is preferably $C_7$-$C_{12}$ arylalkyl group. Examples of arylalkyl groups include, but are not limited to, benzyl, phenethyl, diphenylmethyl, triphenylmethyl, 1-naphthylmethyl, 2-naphthylmethyl, 2,2-diphenylethyl, 3-phenylpropyl, 4-phenylbutyl, and 5-phenylpentyl.

In the present specification, the "$C_4$-$C_{20}$ cycloalkyl group" is preferably $C_4$-$C_{10}$ cycloalkyl group. Examples of cycloalkyl groups include, but are not limited to, cyclopropyl, cyclobutyl, cyclopentyl, and cyclohexyl.

In the present specification, the "$C_4$-$C_{20}$ cycloalkenyl group" is preferably $C_4$-$C_{10}$ cycloalkenyl group. Examples of cycloalkenyl groups include, but are not limited to, cyclopropenyl, cyclobutenyl, cyclopentenyl, and cyclohexenyl.

In the present specification, the "$C_1$-$C_{20}$ alkoxy group" is preferably $C_1$-$C_{10}$ alkoxy group, and more preferably $C_1$-$C_6$ alkoxy group. Examples of alkoxy groups include, but are not limited to, methoxy, ethoxy, propoxy, butoxy, and pentyloxy.

In the present specification, the "$C_6$-$C_{20}$ aryloxy group" is preferably $C_6$-$C_{10}$ aryloxy group. Examples of aryloxy groups include, but are not limited to, phenyloxy, naphthyloxy, and biphenyloxy.

In the present specification, in "alkylthio group (—$SY^1$: in the formula, $Y^1$ is a substituted or unsubstituted $C_1$-$C_{20}$ alkyl group)" and "alkylsulfonyl group (—$SO_2Y^3$: in the formula, $Y^3$ is a substituted or unsubstituted $C_1$-$C_{20}$ alkyl group)", $Y^1$ and $Y^3$ are preferably $C_1$-$C_{10}$ alkyl group, and more preferably $C_1$-$C_6$ alkyl group. Examples of alkyl groups include, but are not limited to, methyl, ethyl, propyl, isopropyl, n-butyl, sec-butyl, tert-butyl, pentyl, hexyl, and dodecanyl.

In the present specification, in "arylthio group (—$SY^2$: in the formula, $Y^2$ is a substituted or unsubstituted $C_6$-$C_{18}$ aryl group)" and "arylsulfonyl group (—$SO_2Y^4$: in the formula, $Y^4$ is a substituted or unsubstituted $C_6$-$C_{18}$ aryl group)", $Y^2$ and $Y^4$ are preferably $C_6$-$C_{10}$ aryl group. Examples of aryl groups include, but are not limited to, phenyl, 1-naphthyl, 2-naphthyl, indenyl, biphenylyl, anthryl, and phenanthryl.

"$C_1$-$C_{20}$ hydrocarbon group," "$C_1$-$C_{20}$ alkoxy group," "$C_6$-$C_{20}$ aryloxy group," "amino group," "silyl group," "alkylthio group," "arylthio group," "alkylsulfonyl group," and "arylsulfonyl group" may be substituted. Examples of substituents in these cases include ester group, carboxyl group, amide group, alkyne group, trimethylsilyl group, amino group, phosphonyl group, thio group, carbonyl group, nitro group, sulfo group, imino group, halogeno group, and alkoxy group. In these cases, one or more substituents (up to the maximum possible number of substituents) may be introduced into replaceable positions, and preferably, 1 to 4 substituents may be introduced. When the number of substituents is 2 or more, the substituents may be the same or different.

In the present specification, examples of "substituted or unsubstituted amino group" include, but are not limited to, amino, dimethylamino, methylamino, methylphenylamino, and phenylamino.

In the present specification, examples of "substituted or unsubstituted silyl group" include, but are not limited to, dimethylsilyl, diethylsilyl, trimethylsilyl, triethylsilyl, trimethoxysilyl, triethoxysilyl, diphenylmethylsilyl, triphenylsilyl, triphenoxysilyl, dimethylmethoxysilyl, dimethylphenoxysilyl, and methylmethoxyphenyl.

In the present specification, examples of "aromatic group" include phenyl group, biphenyl group, and terphenyl group.

In the present specification, examples of "heterocyclic group" include thienyl group, pyrrolyl group, pyridyl group, bipyridyl group, oxazolyl group, oxadiazolyl group, thiazolyl group, thiadiazolyl group, and terthienyl group.

In the present specification, examples of "condensed polycyclic aromatic group" include fluorenyl group, naphthyl group, fluoranthenyl group, anthryl group, phenanthryl group, pyrenyl group, tetracenyl group, pentacenyl group, triphenylenyl group, and perylenyl group.

In the present specification, examples of "condensed polycyclic heterocyclic group" include carbazolyl group, acridinyl group and phenanthroryl group.

Further, examples of substituents which can be had by these "aromatic group," "heterocyclic group," "condensed polycyclic aromatic group" and "condensed polycyclic heterocyclic group" include, but are not limited to, $C_1$-$C_{10}$ hydrocarbon group (e.g., methyl, ethyl, propyl, butyl, phenyl, naphthyl, indenyl, tolyl, xylyl and benzyl), $C_1$-$C_{10}$ alkoxy group (e.g., methoxy, ethoxy, propoxy and butoxy), $C_6$-$C_{10}$ aryloxy group (e.g., phenyloxy, naphthyloxy and biphenyloxy), amino group, hydroxyl group, halogen atom (e.g., fluorine, chlorine, bromine and iodine) and silyl group. In these cases, one or more substituents may be introduced into replaceable positions, and preferably, 1 to 4 substituents may be introduced. When the number of substituents is 2 or more, the substituents may be the same or different.

1.1.2. Method for Producing Fullerene $C_{60}$ Derivative

A method for producing the fullerene derivative having 2 to 4 organic groups which each independently have 1 to 50 carbon atoms (when the fullerene derivative has two organic groups, these organic groups do not bind to each other to form a ring) is not particularly limited. However, the fullerene derivative can be produced using at least one selected from the group consisting of fullerene $C_{60}$ and fullerene $C_{70}$ according to the heretofore known method. For example, a fullerene derivative represented by formula (1) or any one of formulae (1A) to (1G) can be synthesized using: the step of regioselectively adding an organic group to a fullerene (derivative) by reacting at least a Grignard reagent and a polar substance with fullerene $C_{60}$ (organic group addition step A); and the step of adding an organic group by reacting at least a basic compound and a halogen compound (organic group addition step B).

(1) Organic Group Addition Step A

The organic group addition step A is a step of adding an organic group by reacting at least a Grignard reagent and a polar substance with fullerene $C_{60}$.

Grignard Reagent Used in the Organic Group Addition Step A

The Grignard reagent used in the organic group addition step A is represented by the following formula (4):

$$R^6 MgX \quad (4)$$

(wherein: $R^6$ represents an organic group; and X represents Cl, Br or I).

In formula (4), $R^6$ is not particularly limited as long as it is an organic group having a substituent by which the Grignard reagent can be prepared.

In formula (4), $R^6$ is preferably a $C_1$-$C_{20}$ alkyl group, an allyl group, a benzyl group, a 4-methoxybenzyl group, a phenyl group, a 4-methoxyphenyl group, a carbazolylphenyl group, a biphenyl group, a 1-naphthyl group, a pyrenyl group, a di(alkyloxy)benzoyloxyphenyl group or the like.

Further, in formula (4), $R^6$ is preferably a naphthalene tetracarboxylic diimide derivative-containing group, an anthraquinone derivative-containing group, a tetrathiafulvalene derivative-containing group, a polythiophene derivative-containing group or the like.

In formula (4), $R^6$ is preferably a group represented by the following formula (3):

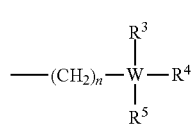

(3)

(wherein in formula (3): W is an atom belonging to group 4B of the periodic table; $R^3$, $R^4$ and $R^5$ are each independently an hydrogen atom, a hydrocarbon group having 1 to 50 carbon atoms, an alkoxy group or an amino group; and n is an integer from 1 to 10).

In formula (3) above, it is preferred that $R^3$, $R^4$ and $R^5$ are each independently a hydrocarbon group having 1 to 20 carbon atoms. It is more preferred that in formula (3), $R^3$ and $R^4$ are methyl and $R^5$ is a hydrocarbon group having 1 to 20 carbon atoms. Further, in formula (3) above, it is preferred that n is an integer from 1 to 5, and W is Si.

In the organic group addition step A, the Grignard reagent is used, preferably in an amount of 1 to 20 equivalents, and more preferably in an amount of 1 to 10 equivalents, of the fullerene or fullerene derivative to which the organic group is added in the organic group addition step A.

According to the preferred embodiment of the present invention, $R^6$ in the above-described formula (4) is to be added to fullerene $C_{60}$ as the starting material.

Polar Substance used in the Organic Group Addition Step A

The polar substance used in the organic group addition step A is not particularly limited as long as it has polar properties, but the donor number (DN) of the polar substance is preferably 25 or more.

As the polar substance used in the organic group addition step A, an aprotic solvent is preferred, and it is more preferred to use N,N-dimethylformamide (DMF), dimethyl sulfoxide (DMSO), pyridine or the like. Among them, N,N-dimethylformamide is particularly preferably used since the yield of a fullerene derivative obtained becomes higher.

In the organic group addition step A, the polar substance is used, preferably in an amount of 3 to 100 equivalents, and more preferably in an amount of 5 to 60 equivalents, of the fullerene or fullerene derivative to which the organic group is added in the organic group addition step A, since the yield of a fullerene derivative obtained becomes higher.

Production of Fullerene Derivative Using the Organic Group Addition Step A

In the organic group addition step A, an organic group is added to fullerene $C_{60}$ by reacting at least the above-described Grignard reagent and the above-described polar substance, thereby producing a fullerene derivative.

The reaction in the organic group addition step A is preferably performed using a solvent. As the solvent, for example, toluene, tetrahydrofuran, dichlorobenzene, a mixed solvent thereof or the like is used. Among them, dichlorobenzene is preferably used as the solvent.

In order to accelerate the reaction in the organic group addition step A, various additives may be used depending on various purposes. Types of catalysts and additives are not particularly limited, and may be suitably selected depending on the type of the starting material or a fullerene derivative to be produced (type of a group to be added).

The reaction system for reacting the Grignard reagent and the polar substance with fullerene $C_{60}$ may be any reaction system, and any of a closed-type system, open-type system and gas-flow-type system may be employed. Further, the reaction method is not particularly limited, and may be appropriately selected in view of types, amounts, etc. of a fullerene, fullerene derivative, Grignard reagent and polar substance to be used.

The addition order of the fullerene $C_{60}$, the Grignard reagent and the polar substance to a reaction tank and the method for the addition thereof may be optionally selected. However, it is preferred that the polar substance is added to a solvent in which the fullerene or fullerene derivative has been dissolved, and thereafter adding the Grignard reagent thereto.

The reaction temperature is generally in the range of −70 to 70° C., and preferably in the range of −50 to 50° C. There is a tendency that, when the reaction temperature is too low, the reaction rate is insufficient, and when the reaction temperature is too high, a side reaction preferentially occurs. The reaction pressure is not particularly limited, and may be ordinary pressure or high pressure. However, ordinary pressure is preferred. The reaction time may be suitably selected depending on the types of the fullerene and organometallic compound to be used, the type of the solvent, the type of the oxidant, the reaction method, etc. In general, the reaction is performed for 2 minutes to 2 hours, and preferably for 5 minutes to 1 hour.

The termination of the reaction is performed, for example, by adding aqueous ammonium chloride solution or the like to the reaction system.

For example, in the organic group addition step A, by reacting at least a Grignard reagent and a polar substance with fullerene $C_{60}$, a fullerene derivative represented by the following formula (2):

$$C_{60}(R^1)(H) \quad (2)$$

(wherein in formula (2), $R^1$ is an organic group having 1 to 50 carbon atoms) is produced.

The synthesized fullerene derivative is not required to be purified if the selective production rate thereof is high. However, there is a case where the fullerene derivative is obtained as a crude product in which by-products such as the raw material fullerene, a slight amount of hydroalkylate and oxide are mixed therewith. Therefore, it is preferred that a fullerene derivative to which a predetermined organic group has been added is isolated/purified from the crude product. Examples of techniques for isolating/purifying a fullerene derivative produced include a technique utilizing chromatography such as HPLC and column chromatography, and a technique of solvent extraction using an organic solvent or the like.

Fullerene Derivative Produced Using the Organic Group Addition Step A

In the organic group addition step A, by reacting at least a Grignard reagent and a polar substance with fullerene $C_{60}$, a fullerene derivative represented by the following formula (2):

$$C_{60}(R^1)(H) \quad (2)$$

(wherein in formula (2), $R^1$ is an organic group having 1 to 50 carbon atoms) is produced.

In the above-described formula (2), $R^1$ is preferably a group represented by the following formula (3):

(3)

(wherein in formula (3): W is an atom belonging to group 4B of the periodic table; $R^3$, $R^4$ and $R^5$ are each independently an hydrogen atom, a hydrocarbon group having 1 to 50 carbon atoms, an alkoxy group or an amino group; and n is an integer from 1 to 10).

In the above-described formula (3), it is preferred that $R^3$, $R^4$ and $R^5$ are each independently a hydrocarbon group having 1 to 20 carbon atoms. It is more preferred that $R^3$ and $R^4$ are methyl and $R^5$ is a hydrocarbon group having 1 to 20 carbon atoms. Further, in the above-described formula (3), preferably, n is an integer from 1 to 5 and W is Si.

(2) Organic Group Addition Step B

The organic group addition step B is, for example, a step of reacting at least a basic compound and a halogen compound with a fullerene derivative represented by the above-described formula (2) obtained in the organic group addition step A to dehydrogenate the fullerene derivative and to add an organic group to the fullerene derivative.

Basic Compound Used in the Organic Group Addition Step B

The basic compound to be used in the organic group addition step B is not particularly limited as long as it is a compound having basicity.

As the basic compound to be used in the organic group addition step B, a metal hydride (e.g., KH, NaH, $CaH_2$), a metal alkoxide (t-BuOK (potassium t-butoxide), t-BuONa (sodium t-butoxide)), an alkali metal reagent (e.g., BuLi), an alkali metal (e.g., K, Na, Li) or an organic alkali (e.g., tetrabutylammonium hydroxide) is preferably used. Among them, a metal alkoxide including Na or K is preferred, and t-BuOK or t-BuONa is particularly preferred.

In the organic group addition step B, the basic compound is used preferably in an amount of 1 to 3 equivalents, and more preferably in an amount of 1 to 2 equivalents of the fullerene derivative to which the organic group is added in the organic group addition step B, since the yield of a fullerene derivative obtained becomes higher.

Halogen Compound Used in the Organic Group Addition Step B

The halogen compound to be used in the organic group addition step B is preferably a compound represented by the following formula (6):

$$R^7X \quad (6)$$

(wherein $R^7$ represents an organic group and X represents a halogen atom). In formula (6), $R^7$ is preferably a $C_1$-$C_{30}$ alkyl group, an allyl group, a benzyl group, a 4-methoxybenzyl group, a phenyl group, a p-methoxyphenyl group, a carbazolylphenyl group, a biphenyl group, a 1-naphthyl group, a pyrenyl group, or a di(alkyloxy)benzoyloxyphenyl group.

Further, in formula (6), $R^7$ is preferably a naphthalene tetracarboxylic diimide derivative-containing group, an anthraquinone derivative-containing group, a tetrathiafulvalene derivative-containing group, a polythiophene derivative-containing group or the like.

In formula (6), $R^7$ is preferably a group represented by the following formula (3):

(3)

(wherein in formula (3): W is an atom belonging to group 4B of the periodic table; $R^3$, $R^4$ and $R^5$ are each independently an hydrogen atom, a hydrocarbon group having 1 to 50 carbon atoms, an alkoxy group or an amino group; and n is an integer from 1 to 10).

In the above-described formula (3), it is preferred that $R^3$, $R^4$ and $R^5$ are each independently a hydrocarbon group having 1 to 20 carbon atoms. It is more preferred that $R^3$ and $R^4$ are methyl and $R^5$ is a hydrocarbon group having 1 to 20 carbon atoms. Further, in the above-described formula (3), it is preferred that n is an integer from 1 to 5 and W is Si.

According to the preferred embodiment, $R^7$ of the above-described formula (6) is to be added to a fullerene derivative to which an organic group is added in the organic group addition step B.

In the organic group addition step B, the halogen compound is used preferably in an amount of 5 to 100 equivalents, and more preferably in an amount of 10 to 50 equivalents of the fullerene derivative to which the organic group is added in the organic group addition step B, since the yield of a fullerene derivative obtained becomes higher.

Production of Fullerene Derivative Using the Organic Group Addition Step B

With a fullerene derivative represented by the above-described formula (2) as the starting material of the organic group addition step B, at least the basic compound and the halogen compound are reacted, thereby adding an organic group to the fullerene derivative (organic group addition step B).

The reaction in the organic group addition step B is preferably performed under inert gas atmosphere using a solvent. As the solvent, a solvent which can dissolve the fullerene derivative as the starting material is preferred, and examples thereof include benzonitrile.

In order to accelerate the reaction in the organic group addition step B, various additives may be used depending on various purposes. Types of catalysts and additives are not particularly limited, and may be suitably selected depending on the type of the starting material or a fullerene derivative to be produced (type of a group to be added).

The reaction system for reacting the basic compound and the halogen compound with the fullerene derivative represented by the above-described formula (2) may be any reaction system, and any of a closed-type system, open-type system and gas-flow-type system may be employed. Further, the reaction method is not particularly limited, and may be appropriately selected in view of types, amounts, etc. of a fullerene derivative, basic compound and halogen compound to be used.

The addition order of the fullerene derivative represented by the above-described formula (2) as the starting material, basic compound and halogen compound to a reaction tank and the method for the addition thereof may be optionally selected. However, it is preferred that the basic compound is added to a solvent in which the fullerene derivative has been dissolved, and thereafter adding the halogen compound thereto. According to the preferred embodiment of the organic group addition step B, the basic compound is added dropwise to the solvent in which the fullerene derivative has been dissolved and the mixture is stirred for 5 to 20 minutes, and after that, the halogen compound is added thereto to cause a reaction in the temperature range of generally 20 to 180° C., and preferably 50 to 150° C., for 2 to 12 hours, and preferably 4 to 10 hours. The reaction pressure is not particularly limited, and may be near ordinary pressure or high pressure. However, near ordinary pressure is preferred.

In the organic group addition step B, by reacting at least the Grignard reagent and the polar substance with the fullerene derivative represented by the above-described formula (2), the fullerene derivative represented by the above-described formula (1), and preferably the fullerene derivative represented by any one of the above-described formulae (1A) to (1G) can be synthesized.

Further, it is preferred that a fullerene derivative synthesized is isolated/purified, and the technique thereof is the same as that in the organic group addition step A.

The fullerene derivative produced by the reaction is not required to be purified if the selective production rate thereof is high. However, purification thereof may be carried out using a technique utilizing chromatography such as HPLC and column chromatography, a technique of solvent extraction using an organic solvent or the like, etc.

1.1.3. Fullerene $C_{70}$ Derivative

One embodiment of the fullerene derivative used as the electron acceptor in the photoelectric conversion device of the present invention is a fullerene $C_{70}$ derivative.

The fullerene $C_{70}$ derivative is a fullerene $C_{70}$ derivative having 2 to 4 organic groups which each independently have 1 to 50 carbon atoms. When the fullerene derivative has two organic groups, these organic groups do not bind to each other to form a ring. The 2 to 4 organic groups added to fullerene $C_{70}$ are the same as the organic groups having 1 to 50 carbon atoms represented by $R^1$ and $R^2$ in the above-described formula (1).

As in the case of the aforementioned fullerene $C_{60}$ derivative, the above-described fullerene $C_{70}$ derivative can be synthesized using: the step of regioselectively adding an organic group to a fullerene (derivative) by reacting at least a Grignard reagent and a polar substance with fullerene $C_{70}$ (organic group addition step A); and the step of adding an organic group by reacting at least a basic compound and a halogen compound (organic group addition step B).

1.2. Compound as the Electron Donor Used in the Photoelectric Conversion Device

The compound as the electron donor used in the photoelectric conversion device of the present invention is not particularly limited as long as it functions as the electron donor.

Note that the compound as the electron donor used in the photoelectric conversion device may be one type of compound or a mixture of a plurality of types of compounds.

The compound as the electron donor used in the present invention is preferably a polymer compound, a porphyrin compound or a phthalocyanine compound.

As the polymer compound to be used as the electron donor, for example, a polymer having an aromatic group such as polythiophene, polypyrrole, polyaniline, polyfuran, polypyridine, polycarbazole and polyphenylene vinylene can be used. Among them, polythiophene, polypyrrole, polyfuran and polyphenylene vinylene are preferred since those to which various substituents are bound exist to provide various structures, allowing synthesis of a large variety of polymers.

Examples of the porphyrin compound to be used as the electron donor include:
5,10,15,20-tetraphenyl-21H,23H-porphin; 5,10,15,20-tetraphenyl-21H,23H-porphin cobalt (II); 5,10,15,20-tetraphenyl-21H,23H-porphin copper (II);
5,10,15,20-tetraphenyl-21H,23H-porphin zinc (II);
5,10,15,20-tetraphenyl-21H,23H-porphine vanadium (IV) oxide;
5,10,15,20-tetra(4-pyridyl)-21H,23H-porphin; and a compound (tetrabenzoporphyrin) represented by the following formula (B):

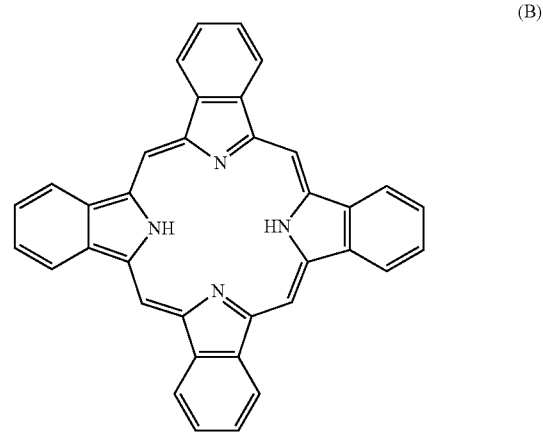 [SMILES: c1ccc2c(c1)-c1cc3[nH]c(cc4nc(cc5[nH]c(cc-2n1)c1ccccc51)-c1ccccc1-4)c1ccccc31]

(B)

Examples of the phthalocyanine compound to be used as the electron donor include: 29H,31H-phthalocyanine; copper phthalocyanine complex; zinc phthalocyanine complex; titanium phthalocyanine oxide complex; magnesium phthalocyanine complex; lead phthalocyanine complex; and copper 4,4',4",4'''-tetraaza-29H,31H-phthalocyanine complex.

Among them, copper phthalocyanine complex is preferred.

1.3. Method for Producing Mixture Layer

In one embodiment of the photoelectric conversion device of the present invention, between a pair of electrodes, a mixture layer consisting of a mixture comprising a fullerene derivative as an electron acceptor and a compound as an electron donor is formed.

The method for producing the mixture layer is not particularly limited. For example, the mixture layer can be produced by applying a solution in which a fullerene derivative and a compound as the electron donor are dissolved to a substrate or a layer provided on a substrate using the spin coat technique or the like (application-type mixture layer). The mixture layer can also be produced by evaporating a fullerene derivative and a compound as the electron donor on a substrate or a layer provided on a substrate (evaporation-type mixture layer).

The fullerene derivative which is preferably used for the application-type mixture layer is a fullerene derivative represented by the above-described formula (1). It is preferred that, in formula (1) or formulae (1A) to (1G), $R^1$ and $R^2$ are each independently a group represented by the following formula (3):

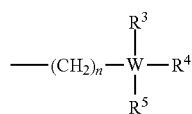

(wherein in formula (3): W is an atom belonging to group 4B of the periodic table; $R^3$, $R^4$ and $R^5$ are each independently an hydrogen atom, a hydrocarbon group having 1 to 50 carbon atoms, an alkoxy group or an amino group; and n is an integer from 1 to 10), since the solubility to a solvent at the time of application is improved and moreover, the conversion efficiency of a photoelectric conversion device obtained is also improved.

It is preferred that in the above-described formula (3), $R^3$, $R^4$ and $R^5$ are each independently a hydrocarbon group having 1 to 20 carbon atoms. It is more preferred that $R^3$ and $R^4$ are methyl and $R^5$ is a hydrocarbon group having 1 to 20 carbon atoms. Further, it is preferred that in the above-described formula (3), n is an integer from 1 to 5 and W is Si.

Though the compound as the electron donor used for the application-type mixture layer is as described above, polythiophene, polypyrrole, polyaniline, polyfuran, polypyridine, polycarbazole polyphenylene vinylene, etc. are preferably used since the conversion efficiency of a photoelectric conversion device obtained is improved.

Moreover, an electron donor obtained from a precursor which can be dissolved in a solvent by means of thermal conversion can also be used for the application-type mixture layer. As such an electron donor, for example, a porphyrin compound or phthalocyanine compound can be used. These compounds are preferably used as the electron donor in the application-type mixture layer since the conversion efficiency of a photoelectric conversion device obtained is improved. Examples of solvents include: aliphatic hydrocarbons such as hexane, heptane, octane, isooctane, nonane and decane; aromatic hydrocarbons such as toluene, benzene, xylene and chlorobenzene; lower alcohols such as methanol, ethanol, propanol and butanol; ketones such as acetone, methyl ethyl ketone, cyclopentanone and cyclohexanone; esters such as ethyl acetate, butyl acetate and methyl lactate; nitrogen-containing organic solvents such as pyridine and quinoline; halogenated hydrocarbons such as chloroform, methylene chloride, dichloroethane, trichloroethane and trichloroethylene; ethers such as ethyl ether, tetrahydrofuran and dioxane; and amides such as dimethylformamide and dimethylacetamide.

Though the compound as the electron donor used in the evaporation-type mixture layer is as described above, a porphyrin compound and a phthalocyanine compound are preferably used since a homogenous layer can be easily provided together with the fullerene derivative and moreover, the conversion efficiency of a photoelectric conversion device obtained is improved.

Note that the mixture layer is not particularly limited as long as it comprises the fullerene derivative and the compound as the electron donor, and it may comprise other compounds, etc.

In addition to the layer of the mixture of the fullerene derivative and the compound as the electron donor, the mixture layer may further comprise: a layer consisting of the electron donor (electron donor layer); a layer consisting of the electron acceptor (electron acceptor layer); or the electron donor layer and the electron acceptor layer.

2. Photoelectric Conversion Device and Solar Cell of the Present Invention

The photoelectric conversion device of the present invention has a substrate and a pair of electrodes, and between the pair of the electrodes, at least a fullerene derivative as an electron acceptor and a compound as an electron donor are provided.

2.1. Substrate

The substrate of the photoelectric conversion device of the present invention serves as a support of the electrodes, etc. Materials of the substrate (substrate materials) are not particularly limited as long as the substrate can serve as the support of the electrodes, etc. However, in the photoelectric conversion device of the present invention, in order to take light irradiated on the substrate into the device, a translucent material is used in the substrate. With respect to the substrate material, the transmission of visible light which permeates the substrate is preferably at least 60%, and more preferably at least 80%.

Preferred examples of the substrate materials include: inorganic materials such as quartz, glass, sapphire and titania; organic materials such as polyethylene terephthalate, polyethylene naphthalate, polyether sulfone, polyimide, nylon, polystyrene, polyvinyl alcohol, ethylene vinyl alcohol copolymer, a fluororesin film, vinyl chloride, polyethylene, cellulose, polyvinylidene chloride, aramid, polyphenylene sulfide, polyurethane, polycarbonate, polyarylate and polynorbornene; paper materials such as paper and synthetic paper; and composite materials such as those in which the surface of a metal such as stainless steel, titanium and aluminum is coated or laminated to provide insulation properties. Among them, glass, polyester, polymethacrylate, polycarbonate and polysulfone are preferred.

As the substrate material, only one type of material may be used, or 2 or more types of materials may be used in any combination at any ratio.

When the gas barrier property of the substrate is low, there is a possibility that an organic photoelectric conversion device 1 may be deteriorated due to external air passing through the substrate. Therefore, when using a material having low gas barrier property (e.g., synthetic resin) as the substrate material, it is preferred that a layer having gas barrier property (gas barrier layer) is formed on one or both of the sides of the substrate. Examples of the gas barrier layer include a dense silicon dioxide film.

There is no limitation on the form of the substrate, and for example, a form such as a plate, film and sheet can be used.

The thickness of the substrate is not particularly limited, but is preferably 5 μm to 20 mm, and more preferably 20 μm to 10 mm. When the substrate is too thin, the strength to hold the organic photoelectric conversion device 1 may be insufficient, and when the substrate is too thick, its cost may be increased or the weight may be too much.

2.2. Electrode

In the photoelectric conversion device of the present invention, materials to be used for electrodes are not particularly limited as long as they have conductive properties. For example, it is preferred that a material having a high work function such as ITO, tin oxide, zinc oxide, Au, Co, Ni and Pt is used in combination with Al, Ag, Li, In, Ca, Mg, LiF or the like. Among them, for an electrode located at a position where light permeates, a transparent electrode such as ITO, tin oxide and zinc oxide is preferably used. A method for producing such electrodes, the thickness thereof, etc. can be suitably selected.

In the photoelectric conversion device of the present invention, when the mixture layer of the fullerene derivative as the electron acceptor and the compound as the electron donor is provided, the thickness of the mixture layer is not particularly limited. However, when the thickness is less than 0.1 nm, the homogeneity is not sufficient, and this causes the problem of tendency of easily occurring short circuit. On the other hand, when the thickness of the mixture layer is more than 5,000 nm, it is not preferred since the internal resistance is increased and the volume percent of the solid layer per device is increased, resulting in reduction of the capacity. Further, the distance between electrodes is increased, and this causes the problem of reduced charge diffusion. Therefore, the thickness of the mixture layer is preferably 0.1 to 5000 nm, more preferably 1 to 1000 nm, and even more preferably 20 to 500 nm.

2.3. p-Type Semiconductor Layer and n-Type Semiconductor Layer

In the photoelectric conversion device of the present invention, a p-type semiconductor layer and an n-type semiconductor layer may be further provided.

(1) p-Type Semiconductor Layer

Between the electrode (positive electrode) and the mixture layer comprising the fullerene derivative as the electron acceptor and the electron donor, a p-type semiconductor layer can be provided.

As a material of the p-type semiconductor layer (p-type semiconductor material), a material by which holes produced in the mixture layer can be efficiently transferred to the positive electrode is preferred. For this purpose, the p-type semiconductor material preferably has the following properties: the hole mobility is high; the conductivity is high; the hole injection barrier between the positive electrode and the p-type semiconductor layer is small; the hole injection barrier from the mixture layer to the p-type semiconductor layer is small; etc.

Further, in the photoelectric conversion device having the p-type semiconductor layer, light is taken into the photoelectric conversion device through the p-type semiconductor layer. Therefore, the p-type semiconductor layer is desired to be transparent. Among lights, usually, visible light is taken into the photoelectric conversion device. Therefore, with respect to a transparent p-type semiconductor material, the transmission of visible light which permeates the p-type semiconductor layer is preferably at least 60%, and more preferably at least 80%.

In order to realize suppression of the production cost of the photoelectric conversion device, an increased area of the device, etc., it is preferred that an organic semiconductor material is used as the p-type semiconductor material to form a p-type organic semiconductor layer as the p-type semiconductor layer.

Preferred examples of the p-type semiconductor material include pigments, and a porphyrin compound or phthalocyanine compound is preferably used. These compounds may have a central metal or may be metal-free. Specific examples thereof include: a phthalocyanine compound such as: 29H, 31H-phthalocyanine; copper (II) phthalocyanine; zinc (II) phthalocyanine; titanium phthalocyanine oxide; and copper (II) 4,4',4'',4'''-tetraaza-29H,31H-phthalocyanine; and a porphyrin compound such as tetrabenzoporphyrin, copper tetrabenzoporphyrin and zinc tetrabenzoporphyrin.

Examples of preferred p-type semiconductor materials other than pigments such as a porphyrin compound and a phthalocyanine compound include a system in which dopant is mixed with a hole-transporting polymer. In this case, examples of hole-transporting polymers include poly(ethylenedioxythiophene), polythiophene, polyaniline and polypyrrole. Examples of dopants include: iodine; acids such as poly(styrene sulfonic acid) and camphor sulfonic acid; and Lewis acids such as $PF_5$, $AsF_5$ and $FeCl_3$.

As the p-type semiconductor material, one type of material may be used solely, or 2 or more types of materials may be used in any combination at any ratio.

There is no limitation on the thickness of the p-type semiconductor layer. However, when the layer is too thick, the transmission may be reduced or the series resistance may be increased. When the layer is too thin, the layer may be an unhomogeneous film. Therefore, the thickness of the p-type semiconductor layer is preferably 3 nm to 200 nm, and more preferably 10 nm to 100 nm. There is no limitation on a method for forming the p-type semiconductor layer. However, when a p-type semiconductor layer comprising a pigment is formed, a method for applying a latent pigment for change is preferred.

(2) n-Type Semiconductor Layer

Between the electrode (negative electrode) and the mixture layer comprising the fullerene derivative as the electron acceptor and the electron donor, an n-type semiconductor layer can be provided.

As a material of the n-type semiconductor layer (n-type semiconductor material), a material by which electrons produced in the mixture layer can be efficiently transferred to the negative electrode is preferred. In order to prevent excitons produced in the mixture layer from being quenched by the negative electrode, it is preferred that the material of the n-type semiconductor layer (n-type semiconductor material) has an optical gap that is larger than an optical gap which the electron donor and the electron acceptor have.

Preferred examples of the n-type semiconductor material include: an organic compound having the electron-transport ability such as a fullerene derivative, a phenanthroline derivative and a silole derivative; and an inorganic semiconductor such as $TiO_2$. As the n-type semiconductor material, one type of material can be used solely, or two or more types of materials can be used in any combination at any ratio.

There is no limitation on the thickness of the n-type semiconductor layer, but the thickness is preferably 2 nm to 200 nm, and more preferably 5 nm to 100 nm.

2.4. Hole Extraction Layer and Electron Extraction Layer

In addition to a pair of electrodes and a fullerene derivative as an electron acceptor and a compound as an electron donor disposed between the electrodes, the photoelectric conversion device of the present invention may further have at least one selected from the group consisting of a hole extraction layer and an electron extraction layer.

The material of the hole extraction layer is not particularly limited as long as it can improve the efficiency of hole extraction from a layer comprising the electron acceptor and the electron donor to an electrode (positive electrode). Specific examples thereof include a conductive organic compound such as polythiophene, polypyrrole, polyacetylene and triphenylene diamine. A thin film of metal or the like such as Au, In, Ag and Pd can also be used. Moreover, the thin film of metal or the like may be formed solely, or may be used in combination with the above-described organic material.

The material of the electron extraction layer is not particularly limited as long as it can improve the efficiency of electron extraction from a layer comprising the electron acceptor and the electron donor to an electrode (negative electrode). Specific examples thereof include a layer in which bathocuproine (BCP), bathophenanthrene (Bphen), or bathocuproine (BCP) and bathophenanthrene (Bphen) are doped with an alkali metal or alkali earth metal. It is also possible to use a fullerene, silole or the like as the material of the electron extraction layer. For example, those in combination with the above-described layer in which bathocuproine (BCP), bathophenanthrene (Bphen), or bathocuproine (BCP) and bathophenanthrene (Bphen) are doped with an alkali metal or alkali earth metal can also be used.

The hole extraction layer and the electron extraction layer are disposed between a pair of electrodes so that the electron acceptor and the electron donor (e.g., the mixture layer, or the mixture layer, n-type semiconductor layer and p-type semiconductor layer) are sandwiched by the layers. That is, when the photoelectric conversion device of the present invention comprises both the hole extraction layer and the electron extraction layer, the device has a structure in which the electrode, the hole extraction layer, the electron acceptor and electron donor (e.g., the mixture layer, or the mixture layer, n-type semiconductor layer and p-type semiconductor layer), the electron extraction layer, and the electrode are disposed in this order. When the photoelectric conversion device of the present invention comprises the hole extraction layer but does not comprise the electron extraction layer, the device has a structure in which the electrode, the hole extraction layer, the electron acceptor and electron donor (e.g., the mixture layer, or the mixture layer, n-type semiconductor layer and p-type semiconductor layer) and the electrode are disposed in this order. When the photoelectric conversion device of the present invention comprises the electron extraction layer but does not comprise the hole extraction layer, the device has a structure in which the electrode, the electron acceptor and electron donor (e.g., the mixture layer, or the mixture layer, n-type semiconductor layer and p-type semiconductor layer), the electron extraction layer and the electrode are disposed in this order.

The fullerene derivative functions as the electron acceptor, and the compound as the electron donor functions as the electron donor. Specifically, when a layer comprising the electron donor and electron acceptor (e.g., mixture layer) is irradiated with light, electrons generated by excitation caused by irradiation move to an opposite electrode through the fullerene derivative in the layer. Further, when electrons move to the fullerene derivative, the compound as the electron donor gets oxidized, and holes move to a working electrode. Current flows in this way.

2.5. Application of Photoelectric Conversion Device

The photoelectric conversion device of the present invention can be suitably used not only in a solar cell, but also in various photoelectric conversion apparatuses such as an optical switching device and a sensor.

EXAMPLES

Hereinafter, the present invention will be specifically described by way of examples and comparative examples. However, the present invention is not limited only to these examples. In the present specification, "Me" represents methyl, and "Ph" represents phenyl.

Synthetic Example 1

Synthesis of $C_{60}(CH_2SiMe_3)H$

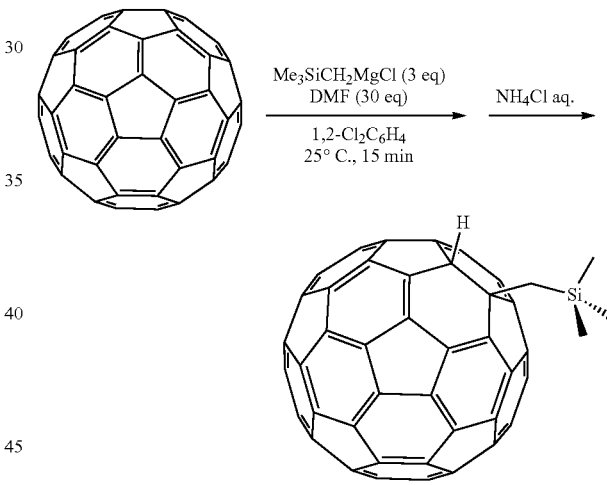

As shown in Scheme 1, to a 50 mL Schlenk flask subjected to deaeration and nitrogen substitution, 50 mg of $C_{60}$ (0.069 mmol, 1.0 eq.) and 5 mL of ODCB (1,2-dichlorobenzene) were added, and the mixture was stirred at room temperature for a while. 155 μL of DMF (2.05 mmol, 30 eq.) was added thereto, and 0.35 mL of 0.592 M trimethylsilylmethyl magnesium chloride/THF solution (0.207 mmol, 3.0 eq.) was added thereto, and the mixture was stirred at room temperature for 15 minutes. The disappearance of the raw material was confirmed by reaction tracking using HPLC (Buckyprep, toluene/2-propanol=7/3), and after that, an aqueous solution of saturated $NH_4Cl$ was added thereto to quench. The reaction solvent was distilled away, and the insoluble was removed using a silica gel short pass (toluene). After that, the solvent was distilled away and reprecipitation was performed using methanol, thereby obtaining 51 mg of fullerene derivative 1 ($C_{60}(CH_2SiMe_3)H$) (yield: 93%; HPLC purity: 91%).

Synthetic Example 2

Synthesis of $C_{60}(CH_2SiMe_3)_2$

Scheme 2

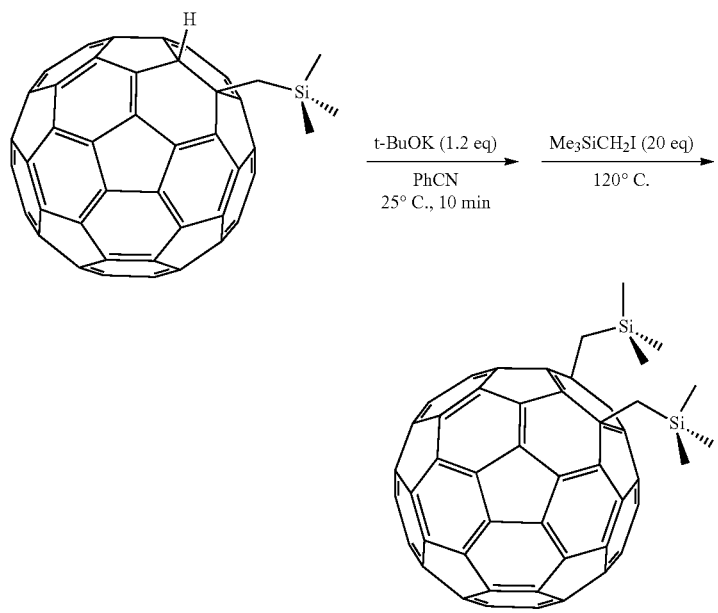

As shown in Scheme 2, to a 50 mL Schlenk flask subjected to deaeration and nitrogen substitution, 20 mg of fullerene derivative 1 synthesized in Synthetic Example 1 ($C_{60}(CH_2SiMe_3)H$) (24.7 μmol, 1.0 eq.) and 4 mL of benzonitrile were added, and the mixture was stirred at room temperature for a while. 29.7 μL of 1.0 M t-BuOK/THF solution (29.7 μmol, 1, 2 eq.) was added thereto, and the mixture was stirred at room temperature for 10 minutes. After that, 73.6 μL of iodomethyl trimethylsilane (0.495 mmol, 20 eq.) was added thereto, and the mixture was stirred at 120° C. for 20 hours. The disappearance of the raw material was confirmed by reaction tracking using HPLC (Buckyprep, toluene/2-propanol=7/3), and after that, the solvent was distilled away, and the insoluble was removed using a silica gel short pass (toluene). After that, purification was performed using column chromatography (silica gel, carbon disulfide/hexane=½) and HPLC (Buckyprep, 20 mm×250 mm, toluene/2-propanol=7/3). The solvent was distilled away, and reprecipitation was performed using methanol, thereby obtaining 20 mg (90%) of fullerene derivative 2 ($C_{60}(CH_2SiMe_3)_2$).

Aside from the aforementioned method, as shown in Scheme 3 below, fullerene derivative 2 ($C_{60}(CH_2SiMe_3)_2$) was obtained.

Scheme 3

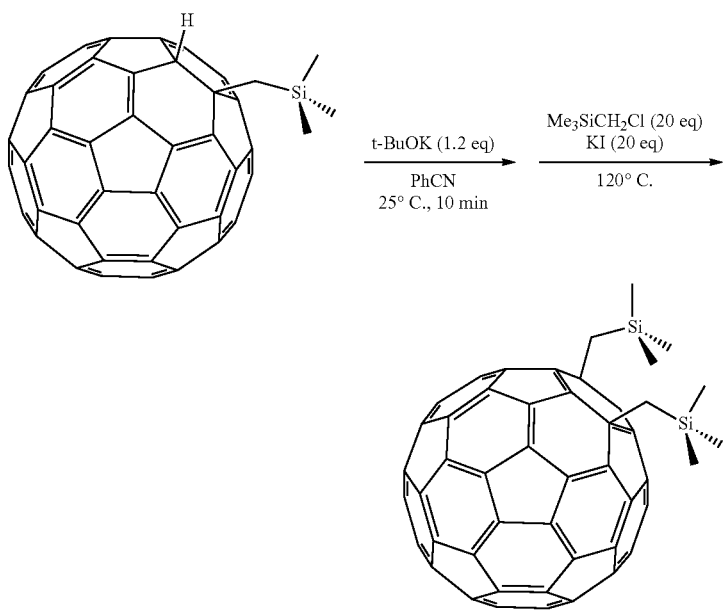

Specifically, as shown in Scheme 3, to a 50 mL Schlenk flask subjected to deaeration and nitrogen substitution, 200 mg of fullerene derivative 1 synthesized in Synthetic Example 1 ($C_{60}(CH_2SiMe_3)H$) (0.25 mmol, 1.0 eq.) and 10 mL of benzonitrile were added, and the mixture was stirred at room temperature for a while. 0.290 mL of 1.0 M t-BuOK/THF solution (0.290 mmol, 1.2 eq.) was added thereto, and the mixture was stirred at room temperature for 10 minutes. After that, 0.427 mL of chloromethyl trimethylsilane (4.94 mmol, 20 eq.) and 820 mg of potassium iodide (4.94 mmol, 20 eq.) were added thereto, and the mixture was stirred at 120° C. for 12 hours. The disappearance of the raw material was confirmed by reaction tracking using HPLC (Buckyprep, toluene/2-propanol=7/3), and after that, the solvent was distilled away and the insoluble was removed using a silica gel short pass (toluene). After that, purification was performed using column chromatography (silica gel, toluene) and HPLC (Buckyprep, 20 mm×250 mm, toluene/2-propanol=7/3). The solvent was distilled away, and reprecipitation was performed using methanol, thereby obtaining 115 mg (51%) of fullerene derivative 2 ($C_{60}(CH_2SiMe_3)_2$).

Synthetic Example 3

Synthesis of $C_{60}(CH_2SiMe_3)(CH_2SiMe_2C_6H_{13})$

As shown in Scheme 4, to a 200 mL Schlenk flask subjected to deaeration and nitrogen substitution, 300 mg of fullerene derivative 1 synthesized in Synthetic Example 1 ($C_{60}(CH_2SiMe_3)H$) (0.371 mmol, 1.0 eq.) and 60 mL of benzonitrile were added, and the mixture was stirred at room temperature for a while. 0.445 mL of 1.0 M t-BuOK/THF solution (0.445 mmol, 1.2 eq.) was added thereto, and the mixture was stirred at room temperature at 10 minutes. After that, 1.43 g of chloromethyl dimethylhexylsilane (7.42 mmol, 20 eq.) and 1.23 g of potassium iodide (7.42 mmol, 20 eq.) were added thereto, and the mixture was stirred at 120° C. for 12 hours. The disappearance of the raw material was confirmed by reaction tracking using HPLC (Buckyprep, toluene/2-propanol=7/3), and after that, the solvent was distilled away and the insoluble was removed using a silica gel short pass (toluene). After that, purification was performed using column chromatography (silica gel, carbon disulfide/hexane=½) and HPLC (Buckyprep, 20 mm×250 mm, toluene/2-propanol=7/3). The solvent was distilled away, and reprecipitation was performed using methanol, thereby obtaining 214 mg (60%) of fullerene derivative 3 ($C_{60}(CH_2SiMe_3)(CH_2SiMe_2C_6H_{13})$).

Scheme 4

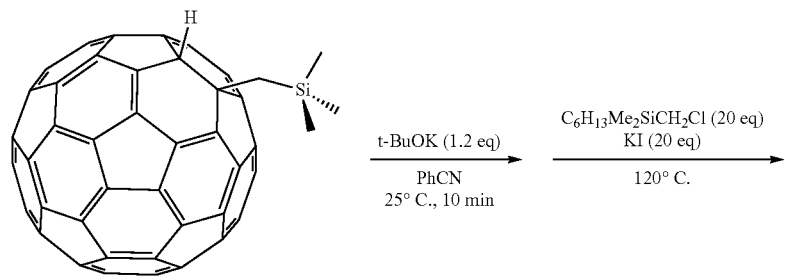

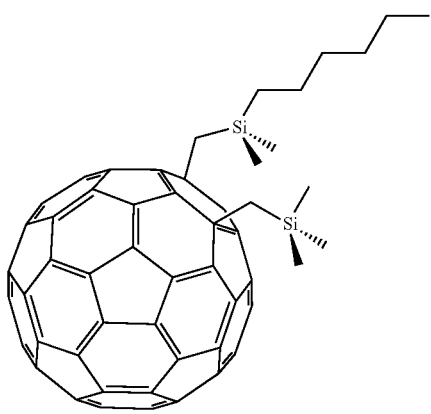

Synthetic Example 4

Synthesis of $C_{60}(CH_2SiMe_3)(CH_2SiMe_2C_{12}H_{25})$

Scheme 5

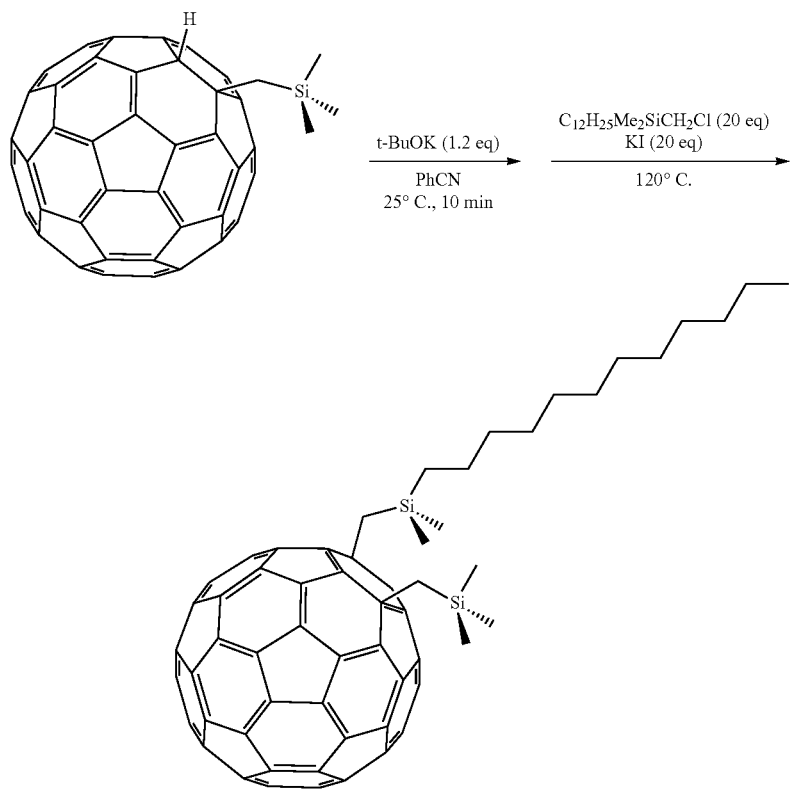

As shown in Scheme 5, to a 200 mL Schlenk flask subjected to deaeration and nitrogen substitution, 500 mg of fullerene derivative 1 synthesized in Synthetic Example 1 ($C_{60}(CH_2SiMe_3)H$) (0.618 mmol, 1.0 eq.) and 100 ml of benzonitrile were added, and the mixture was stirred at room temperature for a while. 0.742 mL of 1.0 M t-BuOK/THF solution (0.742 mmol, 1.2 eq.) was added thereto, and the mixture was stirred at room temperature for 10 minutes. After that, 3.42 g of chloromethyl dimethyldodecylsilane (12.4 mmol, 20 eq.) and 2.05 g of potassium iodide (12.4 mmol, 20 eq.) were added thereto, and the mixture was stirred at 120° C. for 12 hours. The disappearance of the raw material was confirmed by reaction tracking using HPLC (Buckyprep, toluene/2-propanol=7/3), and after that, the solvent was distilled away, and the insoluble was removed using a silica gel short pass (toluene). After that, purification was performed using column chromatography (silica gel, carbon disulfide/hexane=½) and HPLC (Buckyprep, 20 mm×250 mm, toluene/2-propanol=7/3). The solvent was distilled away, and reprecipitation was performed using methanol, thereby obtaining 486 mg (75%) of fullerene derivative 4 ($C_{60}(CH_2SiMe_3)(CH_2SiMe_2C_{12}H_{25})$).

Synthetic Example 5

Synthesis of $C_{60}(CH_2SiMe_2Ph)H$

Scheme 6

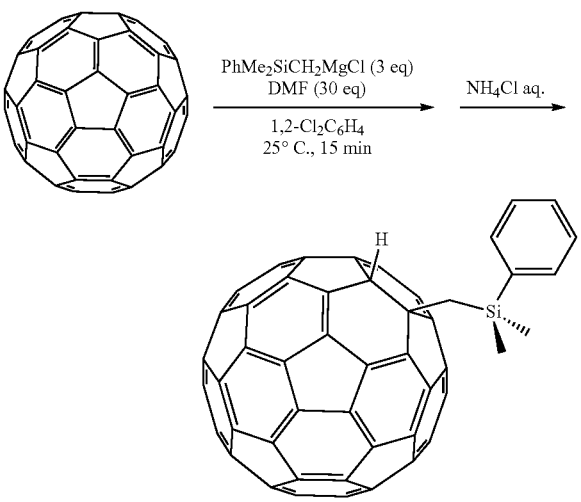

As shown in Scheme 6, to a 2 L flask subjected to deaeration and nitrogen substitution, 5.00 g of $C_{60}$ (6.94 mmol, 1.0 eq.) and 1.00 L of ODCB were added, and the mixture was stirred at room temperature for a while. 15.2 g of DMF (208 mmol, 30 eq.) was added thereto, and 28.4 mL of 0.733 M phenyldimethylsilylmethylmagnesium chloride/THF solution (20.8 mmol, 3.0 eq.) was added thereto, and the mixture was stirred at room temperature for 15 minutes. The disappearance of the raw material was confirmed by reaction tracking using HPLC (Buckyprep, toluene/2-propanol=7/3), and after that, an aqueous solution of saturated NH$_4$Cl was added thereto to perform quench. The reaction solvent was distilled away, and the insoluble was removed using a silica gel short pass (toluene). After that, purification was performed using column chromatography (silica gel, carbon disulfide). After the solvent was distilled away, dissolution in a small amount of toluene was performed, followed by reprecipitation using methanol, thereby obtaining 5.63 g (93%) of fullerene derivative 5 (C$_{60}$(CH$_2$SiMe$_2$Ph)H).

Synthetic Example 6

Synthesis of C$_{60}$(CH$_2$SiMe$_3$)(CH$_2$SiMe$_2$Ph)

Scheme 7

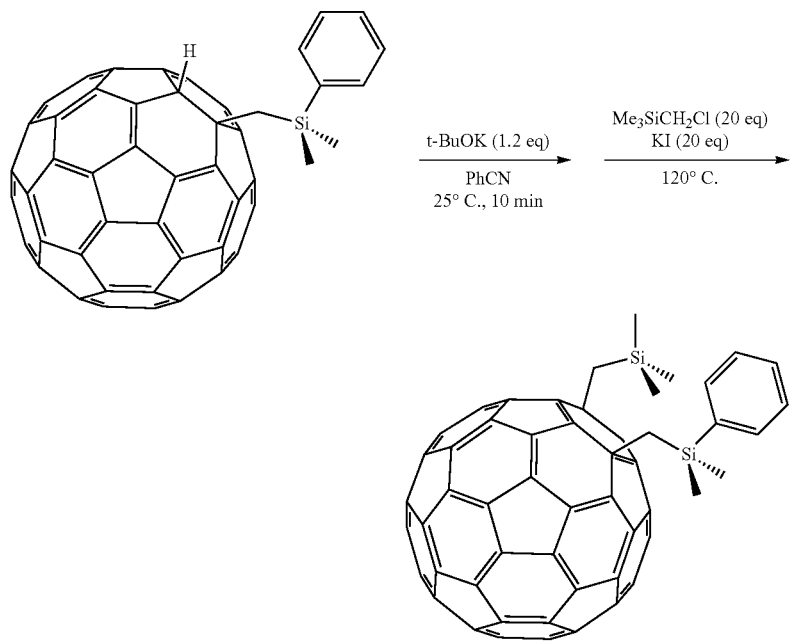

As shown in Scheme 7, to a 200 mL Schlenk flask subjected to deaeration and nitrogen substitution, 1.0 g of fullerene derivative 5 synthesized in Synthetic Example 5 (C$_{60}$(CH$_2$SiMe$_2$Ph)H) (1.15 mmol, 1.0 eq.) and 100 mL of benzonitrile were added, and the mixture was stirred at room temperature for a while. 1.38 mL of 1.0 M t-BuOK/THF solution (1.38 mmol, 1.2 eq.) was added, and the mixture was stirred at room temperature for 10 minutes. After that, 2.82 g of chloromethyl trimethylsilane (23.0 mmol, 20 eq.) and 3.81 g of potassium iodide (23.0 mmol, 20 eq.) were added thereto, and the mixture was stirred at 120° C. for 12 hours. The disappearance of the raw material was confirmed by reaction tracking using HPLC (Buckyprep, toluene/2-propanol=7/3), and after that, the solvent was distilled away, and the insoluble was removed using a silica gel short pass (toluene). After that, purification was performed using HPLC (Buckyprep, 20 mm×250 mm, toluene/2-propanol=7/3). The solvent was distilled away, and reprecipitation was performed using methanol, thereby obtaining 65.1 mg (5.9%) of fullerene derivative 6 (C$_{60}$(CH$_2$SiMe$_3$)(CH$_2$SiMe$_2$Ph)).

Synthetic Example 7

Synthesis of C$_{60}$(CH$_2$SiMe$_2$C$_6$H$_{13}$)H

Scheme 8

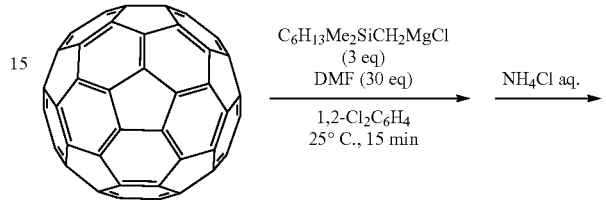

-continued

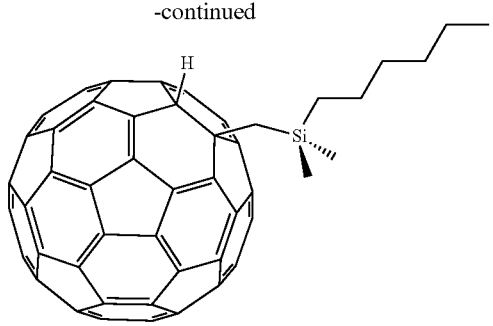

As shown in Scheme 8, to a 200 mL Schlenk flask subjected to deaeration and nitrogen substitution, 2.00 g of C$_{60}$ (2.78 mmol, 1.0 eq.) and 400 mL of ODCB were added, and the mixture was stirred at room temperature for a while. 6.09 g of DMF (83.3 mmol, 30 eq.) was added thereto, and 9.25 mL of 0.90 M hexyldimethyl silylmethyl magnesium chloride/THF solution (8.33 mmol, 3.0 eq.) was added thereto, and the mixture was stirred at room temperature for 15 minutes. The disappearance of the raw material was confirmed by reaction tracking using HPLC (Buckyprep, toluene/2-propanol=7/3), and after that, an aqueous solution of saturated NH$_4$Cl was added thereto to perform quench. The reaction solvent was distilled away, and the insoluble was removed using a silica gel short pass (toluene). After that, the solvent was distilled away and reprecipitation was performed using methanol, thereby obtaining 2.20 g (yield: 90%, HPLC purity: 92%) of fullerene derivative 7 (C$_{60}$(CH$_2$SiMe$_2$C$_6$H$_{13}$)H).

Synthetic Example 8

Synthesis of C$_{60}$(CH$_2$SiMe$_2$C$_6$H$_{13}$)(CH$_2$SiMe$_2$Ph)

As shown in Scheme 9, to a 200 mL Schlenk flask subjected to deaeration and nitrogen substitution, 400 mg of fullerene derivative 7 synthesized in Synthetic Example 7 (C$_{60}$(CH$_2$SiMe$_2$C$_6$H$_{13}$)H) (0.455 mmol, 1.0 eq.) and 80 mL of benzonitrile were added, and the mixture was stirred at room temperature for a while. 0.546 mL of 1.0 M t-BuOK/THF solution (0.546 mmol, 1.2 eq.) was added thereto, and the mixture was stirred at room temperature for 10 minutes. After that, 1.68 g chloromethyl dimethylphenylsilane (9.10 mmol, 20 eq.) and 1.51 g of potassium iodide (9.10 mmol, 20 eq.) were added thereto, and the mixture was stirred at 120° C. for 12 hours. The disappearance of the raw material was confirmed by reaction tracking using HPLC (Buckyprep, toluene/2-propanol=7/3), and after that, the solvent was distilled away, and the insoluble was removed using a silica gel short pass (toluene). After that, purification was performed using column chromatography (silica gel, carbon disulfide/hexane=½) and HPLC (Buckyprep, 20 mm×250 mm, toluene/2-propanol=6/4). The solvent was distilled away, and reprecipitation was performed using methanol, thereby obtaining 358 mg (76%) of fullerene derivative 8 (C$_{60}$(CH$_2$SiMe$_2$C$_6$H$_{13}$)(CH$_2$SiMe$_2$Ph)).

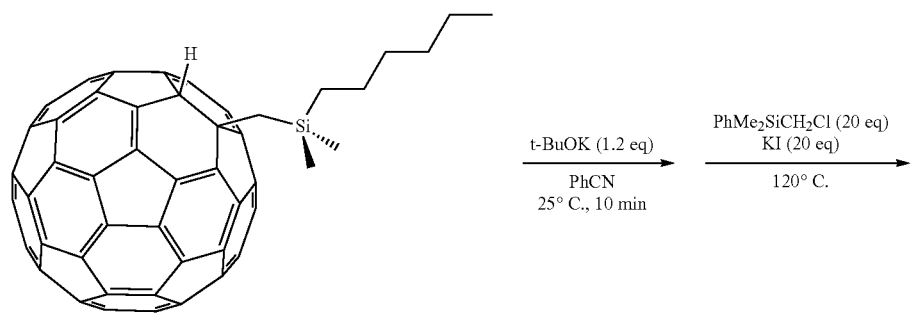

Scheme 9

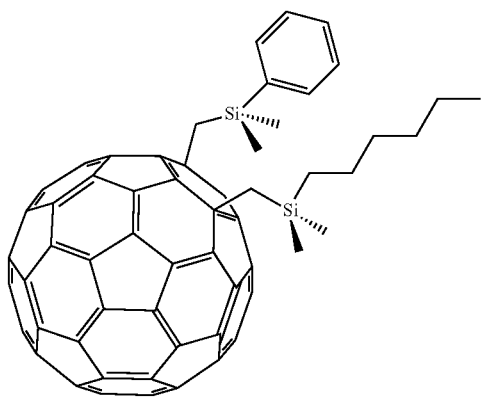

Synthetic Example 9

Synthesis of $C_{60}(CH_2SiMe_2Ph)_2$

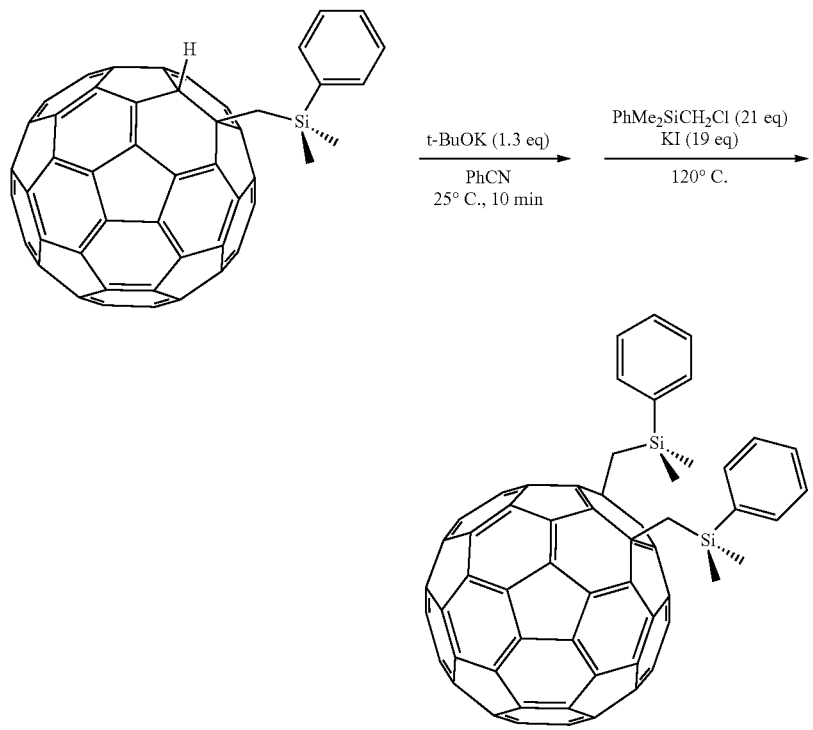

Scheme 10

As shown in Scheme 10, to a 500 mL Schlenk flask subjected to deaeration and nitrogen substitution, 3.01 g of fullerene derivative 5 synthesized in Synthetic Example 5 ($C_{60}(CH_2SiMe_2Ph)H$) (3.45 mmol, 1.0 eq.) and 300 mL of benzonitrile were added, and the mixture was stirred at room temperature (25° C.) for a while. To this reaction system, 4.5 mL of 1.0 M t-BuOK/THF solution (4.50 mmol, 1.3 eq.) was added, and the mixture was stirred at room temperature for 30 minutes. After that, 10.0 g of chloromethyl dimethylphenylsilane (54.1 mmol, 21 eq.) and 11 g of potassium iodide (66.3 mmol, 19 eq.) were added thereto, and the mixture was stirred at 120° C. for 17 hours. The disappearance of the raw material was confirmed by reaction tracking using HPLC (Buckyprep, toluene/2-propanol=7/3), and after that, the solvent was distilled away, and the insoluble was removed using a silica gel short pass (toluene).

The solvent (toluene) was distilled away, and the residue was dissolved in a small amount of chloroform. Reprecipitation was performed using methanol, thereby obtaining 2.55 g (crude yield: 98.5%) of dark brown powdery solid.

After that, purification was performed using column chromatography (silica gel, toluene) and HPLC (Buckyprep, 28 mm×250 mm, toluene; RP FULLERENE, 20 mm×250 mm, toluene/acetonitrile=7/3), and the solvent was distilled away. The residue was dissolved in a small amount of chloroform, and reprecipitation was performed using methanol, thereby obtaining 341.8 mg (13.2%) of fullerene derivative 9 ($C_{60}(CH_2SiMe_2Ph)_2$).

Example 1

Solar Cell Using Fullerene Derivative 2

The constitution of the solar cell of Example 1 is indicated based on FIG. 1, which is a diagram of the solar cell of Example 1. Poly(3-hexylthiophene-2,5-diyl) (Aldrich, trade name: Regioregular) (hereinafter referred to as "P3HT") and fullerene derivative 2 were dissolved in monochlorobenzene so that the weight ratio of P3HT to fullerene derivative 2 became 1:0.8 and the solid content concentration became 2 wt %, thereby preparing a monochlorobenzene solution in which P3HT and fullerene derivative 2 were dissolved.

On an ITO glass substrate in which an ITO electrode 2 as a positive electrode was provided on a glass substrate 1, an aqueous dispersion of poly(3,4)-ethylenedioxythiophene/polystyrene sulfonate (Starck-V TECH Ltd., trade name: "Baytron AI 4083") as a hole extraction layer 3 was applied by spin coating, and thereafter the substrate was subjected to heat treatment on a hot plate. The film thickness was 28 nm. On the substrate after subjected to heat treatment, the aforementioned monochlorobenzene solution was applied by spin coating, thereby obtaining a mixture layer 4 having the film thickness of 89 nm. On the mixture layer 4, an aluminum film having the thickness of 80 nm as an electrode (negative electrode) 5 was provided by means of vacuum deposition, and under nitrogen atmosphere, a transparent glass substrate (not shown) was attached to the ITO glass substrate by a sealant and sealed. This sealed device was subjected to heat treatment on the hot plate at 150° C. for 5 minutes, thereby producing a bulk-heterojunction solar cell shown in FIG. 1.

The produced solar cell was irradiated with light having the intensity of 100 mW/cm2 from the ITO glass substrate side using a solar simulator (AM1.5G), and the current-density-voltage curve between the ITO electrode 2 and the electrode 5 was measured with a source meter (Keithley 2400). Then the photoelectric conversion efficiency was calculated. Results are shown in Table 1.

TABLE 1

| | Fullerene derivative used as electron acceptor | Photoelectric conversion efficiency (%) |
|---|---|---|
| Example 1 | Fullerene derivative 2 | 1.9% |
| Example 2 | Fullerene derivative 3 | 1.8% |
| Example 3 | Fullerene derivative 4 | 1.7% |
| Example 4 | Fullerene derivative 6 | 1.7% |
| Example 5 | Fullerene derivative 8 | 1.4% |
| Example 6 | Fullerene derivative 9 | 3.4% |
| Comparative Example 1 | PCBM | 0.5% |

Example 2

Solar Cell Using Fullerene Derivative 3

A solar cell was produced under the same conditions as those in Example 1, except that fullerene derivative 3 was used instead of fullerene derivative 2. In this case, the film thickness of the mixture layer 4 was 86 nm. With respect to the produced cell, the current-voltage property was measured and the photoelectric conversion efficiency was calculated in a manner similar to that in Example 1. Results are shown in Table 1.

Example 3

Solar Cell Using Fullerene Derivative 4

A solar cell was produced under the same conditions as those in Example 1, except that fullerene derivative 4 was used instead of fullerene derivative 2. In this case, the film thickness of the mixture layer 4 was 81 nm With respect to the produced cell, the current-voltage property was measured and the photoelectric conversion efficiency was calculated in a manner similar to that in Example 1. Results are shown in Table 1.

Example 4

Solar Cell Using Fullerene Derivative 6

A solar cell was produced under the same conditions as those in Example 1, except that fullerene derivative 6 was used instead of fullerene derivative 2. In this case, the film thickness of the mixture layer 4 was 75 nm. With respect to the produced cell, the current-voltage property was measured and the photoelectric conversion efficiency was calculated in a manner similar to that in Example 1. Results are shown in Table 1.

Example 5

Solar Cell Using Fullerene Derivative 8

A solar cell was produced under the same conditions as those in Example 1, except that fullerene derivative 8 was used instead of fullerene derivative 2. In this case, the film thickness of the mixture layer 4 was 65 nm. With respect to the produced cell, the current-voltage property was measured and the photoelectric conversion efficiency was calculated in a manner similar to that in Example 1. Results are shown Table 1.

Example 6

Solar Cell Using Fullerene Derivative 9

Figure 2:
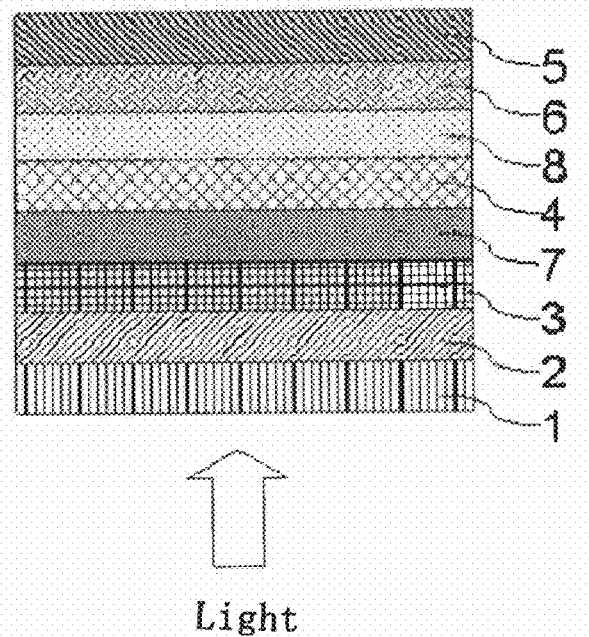
FIG. 2 is a diagram of the solar cell of Example 6.

The constitution of the solar cell of Example 6 is indicated based on FIG. 2, which is a diagram of the solar cell of Example 6.

On an ITO glass substrate in which an ITO electrode 2 as an electrode was provided on a glass substrate 1, an aqueous dispersion of poly(3,4)-ethylenedioxythiophene/polystyrene sulfonate (Starck-V TECH Ltd., trade name: "Baytron PH") as a hole extraction layer 3 was applied by spin coating, and thereafter the substrate was subjected to heat treatment on a hot plate at 120° C. in the atmosphere for 10 minutes. The film thickness was 40 nm.

The substrate was put into a glove box, and under nitrogen atmosphere, the substrate was subjected to heat treatment at 180° C. for 3 minutes. After that, in a mixed solvent of chloroform/monochlorobenzene (1:2, weight), 0.5 wt % of a compound (Compound A) represented by the following formula (A) was dissolved, and the obtained solution was filtered. The obtained filtrate was spin-coated at 1500 rpm and heated at 180° C. for 20 minutes. In this way, on the hole extraction layer 3, a tetrabenzoporphyrin layer as a p-type semiconductor layer 7 was formed.

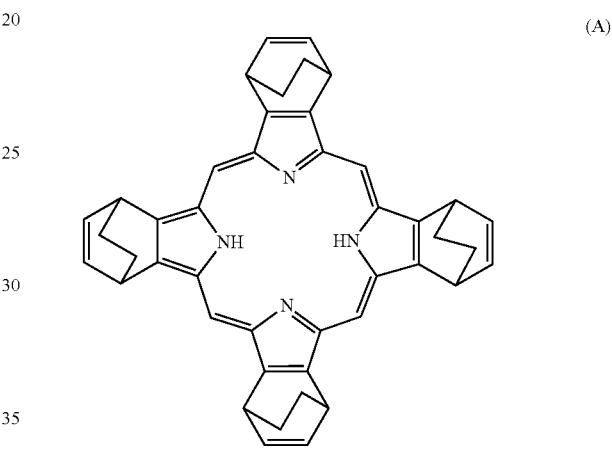

(A)

In a mixed solvent of chloroform/monochlorobenzene (1:1, weight), 0.6 wt % of Compound A and 1.4 wt % of fullerene derivative 9 obtained in Synthetic Example 9 were dissolved, and the prepared solution was filtered. Under nitrogen atmosphere, the obtained filtrate was spin-coated at 1500 rpm and heated at 180° C. for 20 minutes. In this way, on the p-type semiconductor layer 7, a mixture layer 4 of tetrabenzoporphyrin and fullerene derivative 9 was formed.

Next, 1.2 wt % of fullerene derivative 9 was dissolved in toluene, and the prepared solution was filtered. Under nitrogen atmosphere, the obtained filtrate was spin-coated at 3000 rpm and subjected to heat treatment at 65° C. for 10 minutes. The substrate after subjected to heat treatment was placed in a vacuum evaporation apparatus, and air was evacuated using a cryopump. In this way, on the mixture layer 4, an n-type semiconductor layer 8 was formed.

Next, in a metal boat placed in the vacuum evaporation apparatus, a phenanthroline derivative, "bathocuproine" (BCP) was put, and it was heated and evaporated until the film thickness of the phenanthroline derivative, "bathocuproine" (BCP) became 6 nm. Thus, on the n-type semiconductor layer 8, an electron extraction layer 6 was formed.

In addition, on the electron extraction layer 6, an aluminum film having the thickness of 80 nm was provided as an electrode 5 by means of vacuum evaporation. Under nitrogen atmosphere, a transparent glass substrate (not shown) was attached to the ITO glass substrate by a sealant and sealed, thereby producing a solar cell shown in the diagram of FIG. 2.

The produced solar cell was irradiated with light having the intensity of 100 mW/cm2 from the ITO glass substrate side using a solar simulator (AM1.5G), and the current-densityvoltage curve between the ITO electrode 2 and the electrode 5 was measured with a source meter (Keithley 2400). The photoelectric conversion efficiency was calculated, and it was 3.4% (Table 1).

Comparative Example 1

Solar Cell Using PCBM

A solar cell was produced under the same conditions as those in Example 1, except that a fullerene derivative represented by the following formula (5):

(5)

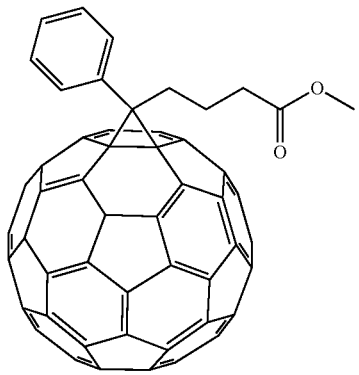

([6,6]-phenyl C61-butyric acid methyl ester) (PCBM) was used instead of fullerene derivative 2.

With respect to the produced cell, the current-density-voltage curve was measured and the photoelectric conversion efficiency was calculated in a manner similar to that in Example 1. Results are shown in Table 1.

INDUSTRIAL APPLICABILITY

The present invention can be utilized, for example, in various photoelectric conversion apparatuses such as solar cells, optical switching devices and sensors.

The invention claimed is:

1. A photoelectric conversion device having at least a fullerene derivative as an electron acceptor represented by any one of the following formulae (1A) to (1G):

(1A)

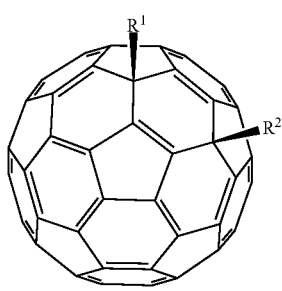

(1B)

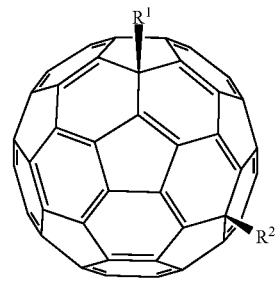

(1C)

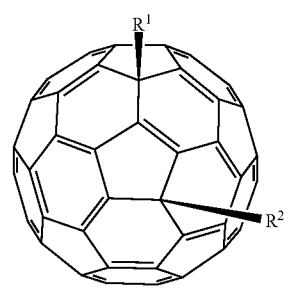

(1D)

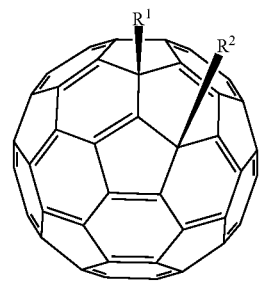

(1E)

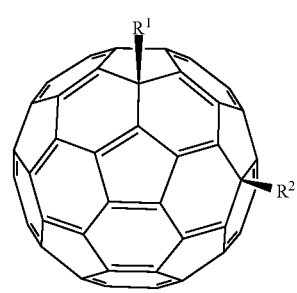

(1F)

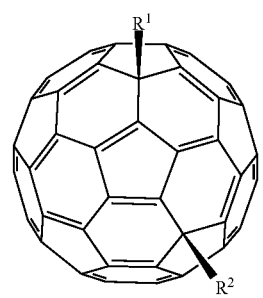

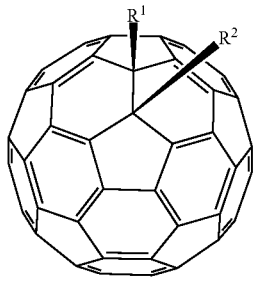

(1G)

wherein in the formulae (1A) to (1G): $R^1$ and $R^2$ are each independently an organic group having 1 to 50 carbon atoms; and $R^1$ and $R^2$ do not bind to each other to form a ring, and a compound as an electron donor between a pair of electrodes, wherein the electron acceptor and electron donor are present in a bulk heterojunction;

wherein one or more of the organic groups having 1 to 50 carbon atoms are each independently a group represented by the following formula (3):

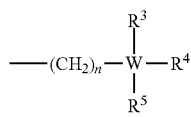

(3)

wherein in the formula (3): W is an atom belonging to group 4B of the periodic table; $R^3$, $R^4$ and $R^5$ are each independently an hydrogen atom, a hydrocarbon group having 1 to 50 carbon atoms, alkoxy or amino; and n is an integer from 1 to 10.

2. The photoelectric conversion device of claim 1, wherein the fullerene derivative is represented by the following formula (1A):

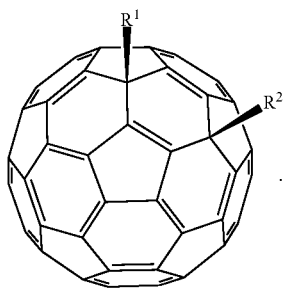

(1A)

3. The photoelectric conversion device according to claim 1, wherein $R^3$, $R^4$ and $R^5$ are each independently a hydrocarbon group having 1 to 20 carbon atoms.

4. The photoelectric conversion device according to claim 1, wherein: $R^3$ and $R^4$ are an alkyl group having 1 to 3 carbon atoms; and $R^5$ is a hydrocarbon group having 1 to 20 carbon atoms.

5. The photoelectric conversion device according to claim 1, wherein: n is an integer from 1 to 5; and W is Si.

6. The photoelectric conversion device according to claim 1, wherein in the formulae (1A) to (1G): $R^1$ is a group represented by the following formula (31):

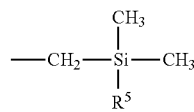

(31)

wherein in the formula (31), $R^5$ is an alkyl group having 1 to 20 carbon atoms or phenyl; and $R^2$ is a group represented by the following formula (32):

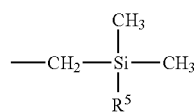

(32)

wherein in the formula (32), $R^5$ is methyl or phenyl.

7. The photoelectric conversion device according to claim 1, wherein the compound as the electron donor is a polymer compound.

8. The photoelectric conversion device according to claim 1, wherein the compound as the electron donor is a heterocyclic polymer compound.

9. The photoelectric conversion device according to claim 1, wherein the compound as the electron donor is a porphyrin compound or phthalocyanine compound.

10. The photoelectric conversion device according to claim 1, wherein the compound as the electron donor is polythiophene or a copper phthalocyanine complex.

11. The photoelectric conversion device according to claim 1, wherein the compound as the electron donor is tetrabenzoporphyrin.

12. The photoelectric conversion device according to claim 1, which has a mixture layer comprising at least the fullerene derivative as the electron acceptor and the compound as the electron donor between the pair of electrodes.

13. The photoelectric conversion device according to claim 12, wherein the mixture layer is formed by applying a solution in which a mixture comprising the fullerene derivative as the electron acceptor and the compound as the electron donor is dissolved.

14. The photoelectric conversion device according to claim 12, wherein the mixture layer is formed by evaporating the fullerene derivative as the electron acceptor and the compound as the electron donor.

15. The photoelectric conversion device according to claim 12, wherein a p-type semiconductor layer is formed between the mixture layer, which comprises the fullerene derivative as the electron acceptor and the electron donor, and a positive electrode.

16. The photoelectric conversion device according to claim 12, wherein an n-type semiconductor layer is formed between the mixture layer, which comprises the fullerene derivative as the electron acceptor and the electron donor, and a negative electrode.

17. A solar cell comprising the photoelectric conversion device according to claim 1.

* * * * *